(12) United States Patent
Merla et al.

(10) Patent No.: US 8,288,424 B2
(45) Date of Patent: Oct. 16, 2012

(54) SUBSTITUTED TETRAHYDROIMIDAZOPYRIDINE COMPOUNDS AND THE USE THEREOF IN THE TREATMENT OF PAIN AND OTHER CONDITIONS

(75) Inventors: Beatrix Merla, Aachen (DE); Stefan Oberboersch, Aachen (DE); Sven Kuehnert, Dueren (DE); Gregor Bahrenberg, Monschau-Konzen (DE); Achim Kless, Aachen (DE)

(73) Assignee: Gruenenthal GmbH, Aachen (DE)

( * ) Notice: Subject to any disclaimer, the term of this patent is extended or adjusted under 35 U.S.C. 154(b) by 743 days.

(21) Appl. No.: 12/356,940

(22) Filed: Jan. 21, 2009

(65) Prior Publication Data
US 2009/0186902 A1 Jul. 23, 2009

(30) Foreign Application Priority Data
Jan. 22, 2008 (EP) ................................. 08001093

(51) Int. Cl.
*A01N 43/50* (2006.01)
*A01N 43/52* (2006.01)
*A61K 31/415* (2006.01)

(52) U.S. Cl. ........................................ 514/385; 514/393
(58) Field of Classification Search .................. 514/387, 514/385, 393
See application file for complete search history.

(56) References Cited

U.S. PATENT DOCUMENTS

| 2002/0128277 A1 | 9/2002 | Dworetzky et al. |
| 2005/0154202 A1 | 7/2005 | Hagmann et al. |
| 2008/0051409 A1 | 2/2008 | Gmeiner et al. |

FOREIGN PATENT DOCUMENTS

| DE | 10 2004 037 445 A1 | 3/2006 |
| GB | 1 473 819 | 5/1977 |
| WO | WO 2004/024074 A2 | 3/2004 |
| WO | WO 2006/015737 A1 | 2/2006 |

OTHER PUBLICATIONS

PCT/ISA/237 form (nine (9) pages).

Gordon Blackburn-Munro, et al., "The anticonvulsant retigabine attenuates nociceptive behaviours in rat models of persistent and neuropathic pain", European Journal of Pharmacology, 2003, vol. 406 pp. 109-116.
Giovambattista De Sarro, et al."Influence of retigabine on the anticonvulsant activity of some antiepileptic drugs against audiogenic seizures in DBA/2 mice", Naunyn-Schmiedeberg's Arch Pharmacol, 2001, vol. 363, pp. 330-336.
R Dost, et al., "The anti-hyperalgesic activity of retigabine is mediated by KCNQ potassium channel activation", Naunyn-Schmiedeberg's Arch Pharmacol, 2004, vol. 369, pp. 382-390.
Valentin K. Gribkoff, "The therapeutic potential of neuronal KCNQ channel modulators", Expert Opin. Ther. Targets, 2003, vol. 7, No. 6, pp. 737-748.
M. P. G. Korsgaard, et al., "Anxiolytic Effects of Maxipost (BMS-204352) and Retigabine via Activation of Neuronal $K_v7$ Channels", The Journal of Pharmacology and Experimental Therapeutics, The American Society for Pharmacology and Experimental Therapeutics, 2005, vol. 314, pp. 282-292.
Alexander Norup Nielsen, et al. "Pharmacological characterisation of acid-induced muscle allodynia in rats", European Journal of Pharmacology, 2004, vol. 487, pp. 93-103.
Gayle M. Passmore, et al., "KCNQ/M Currents in Sensory Neurons: Significance for Pain Therapy", The Journal of Neuroscience, Aug. 6, 2003, vol. 23, No. 18, pp. 7227-7236.
Tomi Streng, et al., "Urodynamic Effects of the K+ Channel (KCNQ) Opener Retigabine in Freely Moving, Conscious Rats", Nov. 2004, vol. 172, pp. 2054-2058.
Alan D. Wickenden, et al., "KCNQ potassium channels: drug targets for the treatment of epilepsy and pain", Expert. Opin. Ther. Patents, 2004, vol. 14, No. 4, pp. 457-469.
European Search Report including partial translation dated Sep. 4, 2008 (Eight (8) pages).

*Primary Examiner* — Yong Chong
(74) *Attorney, Agent, or Firm* — Crowell & Moring LLP

(57) ABSTRACT

Substituted tetrahydroimidazopyridine compounds corresponding to formula I:

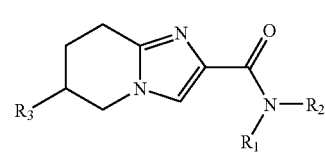

in which $R^1$, $R^2$ and $R^3$ have defined meanings, processes for preparing such compounds, pharmaceutical compositions containing such compounds, and the use of such compounds for treating or inhibiting pain, epilepsy, migraine, anxiety or urinary incontinence.

17 Claims, No Drawings

SUBSTITUTED TETRAHYDROIMIDAZOPYRIDINE COMPOUNDS AND THE USE THEREOF IN THE TREATMENT OF PAIN AND OTHER CONDITIONS

CROSS REFERENCE TO RELATED APPLICATIONS

This application claims priority from European patent application no. EP 008001093.7, filed Jan. 22, 2008, the entire disclosure of which is incorporated herein by reference.

BACKGROUND OF THE INVENTION

The present invention relates to substituted tetrahydroimidazopyridine compounds, processes for the preparation thereof, pharmaceutical compositions containing these compounds, and the use of these compounds for the preparation of medicinal products and the treatment or inhibition of pain and other conditions.

The treatment of pain, in particular neuropathic pain, is of great importance in medicine. There is a worldwide need for effective pain therapies. The urgent need for action to find targeted, patient-appropriate treatment for chronic and non-chronic pain conditions, this being understood as the successful and satisfactory treatment of pain for the patient, is also documented in the large number of scientific works that have been published in recent times in the field of applied analgesics and basic research into nociception.

A pathophysiological feature of chronic pain is the over-excitability of neurons. Neuronal excitability is decisively influenced by the activity of $K^+$ channels, since these significantly determine the resting potential of the cell and hence the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarisation of the cell membrane and, accompanying this, to a decrease in the electrical excitability of these neurons. KCNQ2/3-expressing neurons of the dorsal root ganglia are involved in the transmission of nociceptive stimuli from the periphery into the spinal cord (Passmore et al., J. Neurosci. 2003; 23(18):7227-36). It has accordingly been possible to detect an analgesic activity in preclinical neuropathic and inflammatory pain models for the KCNQ2/3 agonist retigabine (Blackburn-Munro and Jensen, Eur J. Pharmacol. 2003; 460(2-3):109-16; post et al., Naunyn Schmiedeberg's Arch Pharmacol 2004; 369(4): 382-390). The KCNQ2/3 $K^+$ channel thus represents a suitable starting point for the treatment of pain; in particular pain chosen from the group consisting of chronic pain, neuropathic pain, inflammatory pain and muscular pain (Nielsen et al., Eur J. Pharmacol. 2004; 487(1-3): 93-103), in particular neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety states (Korsgaard et al., J Pharmacol Exp Ther. 2005, 14(1): 282-92), epilepsy (Wickenden et al., Expert Opin Ther Pat 2004; 14(4): 457-469) and urinary incontinence (Streng et al., J Urol 2004; 172: 2054-2058).

SUMMARY OF THE INVENTION

An object of the present invention was therefore to provide novel compounds which are suitable in particular as pharmacological active ingredients in medicinal products, preferably in medicinal products for the treatment of disorders or diseases which are at least partly mediated by KCNQ2/3 $K^+$ channels.

Surprisingly it has now been found that substituted tetrahydroimidazopyridine compounds having the general formula I given below are suitable for the treatment of pain and also have an excellent affinity for the KCNQ2/3 $K^+$ channel and are therefore suitable for the treatment of disorders or diseases which are at least partly mediated by KCNQ2/3 $K^+$ channels.

WO 2006/015737 discloses a large number of compounds, among them substituted tetrahydroimidazopyridines. These compounds are dopamine receptor ligands; in these compounds, however, the amide-nitrogen is always bound to a phenyl-substituted piperazine via an alkyl or cycloalkyl bridge.

The invention therefore provides substituted tetrahydroimidazopyridine compounds having the general formula I,

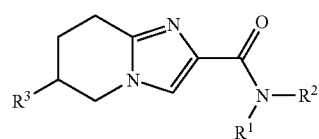

wherein
$R^1$ and $R^2$ each independently denote H; $C_{1-10}$ alkyl, $C_{1-4}$ alkyl aryl, $C_{1-4}$ alkyl heteroaryl, $C_{1-4}$ alkyl $C_{3-8}$ cycloalkyl, $C_{1-4}$ alkyl heterocyclyl or $C_{3-8}$ cycloalkyl, wherein the alkyl, aryl, heteroaryl, heterocyclyl and cycloalkyl groups may each be unsubstituted or mono- or polysubstituted, and $R^1$ and $R^2$ do not simultaneously denote H; or
$R^1$ and $R^2$ together with the nitrogen to which they are bound form a four- to eight-membered heterocyclic ring, optionally bridged by a $C_1$ or $C_2$ alkyl chain, which may contain a further heteroatom and may be substituted or unsubstituted; and
$R^3$ denotes unsubstituted or mono- or polysubstituted phenyl; with the proviso that if one of $R^1$ or $R^2$ denotes H, alkyl or phenyl alkyl, the other one of $R^1$ or $R^2$ does not denote a group having the formula X1

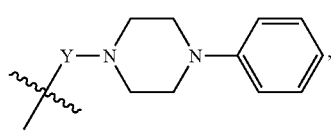

wherein the phenyl group in formula X1 may be unsubstituted or substituted, and
Y denotes a $C_{2-5}$ alkyl chain or —$(CH_2)_o$-Z-$(CH_2)_p$—,
wherein Z denotes cyclopentyl, cyclohexyl or cycloheptyl, and
o and p are each 0, 1, 2 or 3, with the sum of o and p being less than or equal to 3; in the form of the racemate; the enantiomers, diastereomers, mixtures of enantiomers or diastereomers or a single enantiomer or diastereomer; the bases and/or salts of physiologically compatible acids.

Within the meaning of this invention the expressions "$C_{1-4}$ alkyl" and "$C_{1-10}$ alkyl" include acyclic saturated or unsaturated hydrocarbon groups, which can be branched or straight-chain and unsubstituted or mono- or polysubstituted, having respectively 1 to 4 C atoms or 1 to 10 C atoms, i.e. $C_{1-4}$ alkanyls, $C_{2-4}$ alkenyls and $C_{2-4}$ alkynyls or $C_{1-10}$ alkanyls, $C_{2-10}$ alkenyls and $C_{2-10}$ alkynyls. Alkenyls have at least one C—C double bond and alkynyls have at least one C≡C triple bond. Alkyl is advantageously selected from the group comprising methyl, ethyl, n-propyl, 2-propyl, n-butyl, isobutyl, sec-butyl, tert-butyl, n-pentyl, isopentyl, neopentyl, hexyl, ethylenyl (vinyl), ethynyl, propenyl (—$CH_2CH$=$CH_2$, —CH=CH—$CH_3$, —C(=$CH_2$)—$CH_3$), propynyl (—CH—C≡CH, —C≡C—$CH_3$), butenyl, butynyl, pentenyl, pentynyl, hexenyl and hexynyl. Methyl, ethyl, n-propyl and n-butyl are particularly advantageous.

For the purposes of this invention the expression "cycloalkyl" or "$C_{3-8}$ cycloalkyl" denotes cyclic hydrocarbons having 3, 4, 5, 6, 7 or 8 carbon atoms, which can optionally also be bridged, wherein the hydrocarbons can be saturated or unsaturated (but not aromatic), unsubstituted or mono- or polysubstituted. $C_{3-8}$ cycloalkyl is advantageously selected from the group including cyclopropyl, cyclobutyl, cyclopentyl, cyclohexyl, cycloheptyl, cyclooctyl, cyclopentenyl, cyclohexenyl, cycloheptenyl and cyclooctenyl.

The term "heterocyclyl" comprises saturated or unsaturated (but not aromatic) cycloalkyls having three to ten, preferably four to eight, ring members, which can optionally also be bridged, in which one or two carbon atoms are replaced by an S, N or O heteroatom. Heterocyclyl groups are advantageously selected from the group consisting of tetrahydropyranyl, azabicyclo[3.2.1]octane, dioxanyl, dioxolanyl, morpholinyl, piperidinyl, pyrazolinonyl and pyrrolidinyl.

Within the meaning of this invention, the expression "aryl" denotes aromatic hydrocarbons having up to 14 ring members, inter alia phenyls and naphthyls. The aryl groups can also be fused to other saturated, (partially) unsaturated or aromatic ring systems. Each aryl group can be present in unsubstituted or mono- or polysubstituted form, wherein the aryl substituents can be identical or different and can be at any desired and possible position of the aryl. Aryl is advantageously selected from the group including phenyl, 1-naphthyl, 2-naphthyl, each of which can be unsubstituted or mono- or polysubstituted.

The expression "heteroaryl" denotes a 5-, 6- or 7-membered cyclic aromatic group containing at least 1, optionally also 2, 3, 4 or 5 heteroatoms, wherein the heteroatoms can be identical or different and the heterocyclic compound can be unsubstituted or mono- or polysubstituted; if the heterocyclic compound is substituted, the substituents can be identical or different and can be at any desired and possible position of the heteroaryl. The heterocyclic compound can also be part of a bicyclic or polycyclic system having up to 14 ring members. Preferred heteroatoms are nitrogen, oxygen and sulfur. It is preferable for the heteroaryl group to be selected from the group including pyrrolyl, indolyl, furyl (furanyl), benzofuranyl, thienyl (thiophenyl), benzothienyl, benzothiadiazolyl, benzothiazolyl, benzotriazolyl, phthalazinyl, pyrazolyl, imidazolyl, thiazolyl, oxadiazolyl, isoxazolyl, oxazolyl, triazolyl, pyridyl, pyridazinyl, pyrimidinyl, pyrazinyl, indazolyl, purinyl, indolizinyl, quinolinyl, isoquinolinyl, quinazolinyl, carbazolyl, phenazinyl, wherein the bond to the compounds having the general structure I can be made via any desired and possible ring member of the heteroaryl group. Pyridyl, furyl and thienyl are particularly preferred.

For the purposes of the present invention the expression "aryl, heteroaryl, heterocyclyl or cycloalkyl bound by $C_{1-4}$ alkyl" means that $C_{1-4}$ alkyl and aryl or heteroaryl or heterocyclyl or cycloalkyl have the meanings defined above and the aryl or heteroaryl or heterocyclyl or cycloalkyl group is bound to the compound having the general structure I by a $C_{1-4}$ alkyl group. The alkyl chain can in all cases be saturated or unsaturated, branched or unbranched, unsubstituted or mono- or polysubstituted. It is advantageous for the alkyl chain to be unsubstituted or substituted with a methyl group. Phenyl, benzyl and phenethyl are particularly advantageous within the meaning of this invention.

In connection with "alkyl", "heterocyclyl" and "cycloalkyl" the term "substituted" within the meaning of this invention is understood to mean the substitution of a hydrogen group with F, Cl, Br, I, —CN, $NH_2$, NH—$C_{1-6}$ alkyl, NH—$C_{1-6}$ alkyl-OH, $C_{1-6}$ alkyl, N($C_{1-6}$ alkyl)$_2$, N($C_{1-6}$ alkyl-OH)$_2$, $NO_2$, SH, S—$C_{1-6}$ alkyl, S-benzyl, O—$C_{1-6}$ alkyl, OH, O—$C_{1-6}$ alkyl-OH, =O, O-benzyl, C(=O)$C_{1-6}$ alkyl, C(=O)O$C_{1-6}$ alkyl, phenyl or benzyl, wherein a substituent can optionally itself be substituted, but not with a further aryl or heteroaryl ring. Polysubstituted groups are understood to mean groups which are either substituted multiple times, e.g. twice or three times, at different or the same atoms, for example three times at the same C atom, as in the case of $CF_3$ or —$CH_2CF_3$, or at different sites, as in the case of —CH (OH)—CH=CH—$CHCl_2$. The polysubstitution can be performed with identical or different substituents.

With reference to "aryl", "phenyl" and "heteroaryl", within the meaning of this invention "mono- or polysubstituted" is understood to mean the mono- or poly- (i.e. di-, tri- or tetra-) substitution of one or more hydrogen atoms of the ring system with F, Cl, Br, I, CN, $NH_2$, NH—$C_{1-6}$ alkyl, NH—$C_{1-6}$ alkyl-OH, N($C_{1-6}$ alkyl)$_2$, N($C_{1-6}$ alkyl-OH)$_2$, $NO_2$, SH, S—$C_{1-6}$ alkyl, OH, O—$C_{1-6}$ alkyl, O—$C_{1-6}$ alkyl-OH, C(=O)$C_{1-6}$ alkyl, C(=O)NH$C_{1-6}$ alkyl; C(=O) aryl; C(=O)—N-morpholine; C(=O)-piperidine; (C=O)-pyrrolidine; (C=O)-piperazine; $NHSO_2C_{1-6}$ alkyl, $NHCOC_{1-6}$ alkyl, $CO_2H$, $CH_2SO_2$ phenyl, $CO_2$—$C_{1-6}$ alkyl, $OCF_3$, $SCF_3$, $CF_3$,

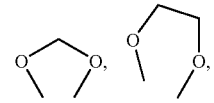

$C_{1-6}$ alkyl, pyrrolidinyl, piperidinyl, morpholinyl, benzyloxy, phenoxy, phenyl, pyridyl, alkylaryl, thienyl or furyl; at one or optionally different atoms, wherein a substituent can optionally itself be substituted, but not with a further aryl or heteroaryl ring. The polysubstitution is performed with identical or with different substituents. Preferred substituents for "aryl" or "heteroaryl" are F, Cl, $OCH_3$, $CF_3$, $OCF_3$, $SCF_3$ and $CH_3$.

Within the meaning of this invention the term "salt formed with a physiologically compatible acid" is understood to mean salts of the individual active ingredient with inorganic or organic acids which are physiologically—particularly when used in humans and/or mammals—compatible. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro-$1\lambda^6$-benzo[d]isothiazol-3-one (saccharinic acid), monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. Citric acid and hydrochloric acid are particularly preferred.

Preferred within the meaning of this invention are substituted tetrahydroimidazopyridine compounds having the general formula I, wherein "alkyl substituted", "heterocyclyl substituted" and "cycloalkyl substituted" denotes the substitution of a hydrogen group with F, Cl, Br, I, —CN, $NH_2$, NH—$C_{1-6}$ alkyl, NH—$C_{1-6}$ alkyl-OH, $C_{1-6}$ alkyl, $N(C_{1-6}$ alkyl$)_2$, $N(C_{1-6}$ alkyl-OH$)_2$, $NO_2$, SH, S—$C_{1-6}$ alkyl, S-benzyl, O—$C_{1-6}$ alkyl, OH, O—$C_{1-6}$ alkyl-OH, =O, O-benzyl, C(=O)$C_{1-6}$ alkyl, C(=O)O$C_{1-6}$ alkyl, phenyl or benzyl, and "aryl substituted", "phenyl substituted" and "heteroaryl substituted" denotes the single or multiple, e.g. two, three or four times, substitution of one or more hydrogen atoms in the ring system with F, Cl, Br, I, CN, $NH_2$, NH—$C_{1-6}$ alkyl, NH—$C_{1-6}$ alkyl-OH, $N(C_{1-6}$ alkyl$)_2$, $N(C_{1-6}$ alkyl-OH$)_2$, $NO_2$, SH, S—$C_{1-6}$ alkyl, OH, O—$C_{1-6}$ alkyl, O—$C_{1-6}$ alkyl-OH, C(=O) aryl; C(=O)$C_{1-6}$ alkyl, C(=O)NH$C_{1-6}$ alkyl; C(=O)—N-morpholine; C(=O)-piperidine; (C=O)-pyrrolidine; (C=O)-piperazine; $NHSO_2C_{1-6}$ alkyl, NHCO$C_{1-6}$ alkyl, $CO_2H$, $CH_2SO_2$ phenyl, $CO_2$—$C_{1-6}$ alkyl, $OCF_3$, $CF_3$,

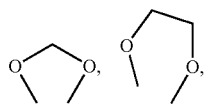

$C_{1-6}$ alkyl, pyrrolidinyl, piperidinyl, morpholinyl, benzyloxy, phenoxy, phenyl, pyridyl, alkylaryl, thienyl or furyl.

The groups $C_{1-6}$ alkyl, pyrrolidinyl, piperidinyl, morpholinyl, benzyloxy, phenoxy, phenyl, pyridyl, alkylaryl, thienyl or furyl can themselves be substituted with F, Cl, methoxy, ethoxy, $CF_3$, CN, $CH_3$, OH, $OCF_3$, $SCF_3$ or $NO_2$.

Also preferred within the meaning of this invention are substituted tetrahydroimidazopyridine compounds having the general formula I, wherein $R^1$ and $R^2$ each independently denote $C_{1-10}$ alkyl, $C_{1-4}$ alkyl aryl, $C_{1-4}$ alkyl heteroaryl, $C_{1-4}$ alkyl $C_{3-8}$ cycloalkyl or $C_{3-8}$ cycloalkyl, wherein the alkyl, aryl, heteroaryl and cycloalkyl groups may each be unsubstituted or mono- or polysubstituted.

Also preferred are substituted tetrahydroimidazopyridine compounds having the general formula I, wherein $R^1$ and $R^2$ together with the nitrogen atom to which they are bound form a four- to eight-membered ring, optionally bridged by a $C_1$ or $C_2$ alkyl chain, which may contain a further heteroatom selected from the group consisting of O, N and S and which may be substituted or unsubstituted.

Particularly preferred are substituted tetrahydroimidazopyridine compounds having the general formula I, wherein $R^1$ and $R^2$ each independently denote H; benzyl, phenethyl, methylpyridyl, cyclopropyl, n-pentyl, n-butyl, n-hexyl, sec-butyl, propylethyl or methylcyclohexyl, each of which may be unsubstituted or mono- or polysubstituted with methoxy, F, $CH_3$, $CF_3$ or

in particular benzyl, phenethyl, methylpyridyl, cyclopropyl, 3,4-dimethoxyphenethyl, benzo[1,3]dioxol-5-yl, 4-fluorobenzyl, (1-methyl)propylphenyl, 3-trifluoromethylbenzyl, sec-butyl, (1-methyl)benzyl, methylcyclohexyl or (1-methyl)-3,4-dimethylbenzyl, n-butyl, n-pentyl or n-hexyl.

Also particularly preferred are substituted tetrahydroimidazopyridine compounds having the general formula I, wherein $R^1$ and $R^2$ together with the nitrogen atom to which they are bound form a five- to seven-membered ring which may contain a further nitrogen atom and which may be unsubstituted or mono- or polysubstituted with C(O)O$C_2H_5$; C(O) $C_{1-6}$ alkyl; methyl, n-butyl or acetyl; phenyl or benzyl, each unsubstituted or substituted with phenyl F, Cl, Br, I, CN, $CH_3$, $C_2H_5$, $NH_2$, $NO_2$, SH, $CF_3$, OH, $OCH_3$, $OCF_3$, $SCF_3$, $SCH_3$, $OC_2H_5$ or $N(CH_3)_2$.

Most particularly preferred are substituted tetrahydroimidazopyridine compounds having the general formula I, wherein the $NR^1R^2$ grouping denotes

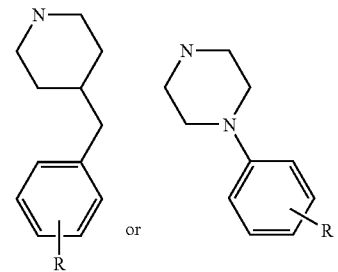

wherein R denotes H, phenyl F, Cl, Br, I, CN, $CH_3$, $C_2H_5$, $NH_2$, $NO_2$, SH, $CF_3$, OH, $OCH_3$, $OCF_3$, $SCF_3$, $SCH_3$, $OC_2H_5$ or $N(CH_3)_2$; in particular

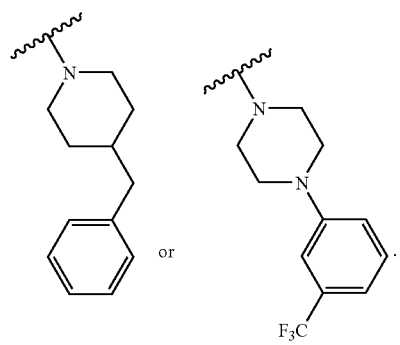

Also preferred are tetrahydroimidazopyridine derivatives wherein $R^3$ denotes phenyl, unsubstituted or mono- or polysubstituted with F, Cl, Br, I, CN, $CH_3$, $C_2H_5$, $NH_2$, $NO_2$, SH, $CF_3$, OH, $OCH_3$, $OCF_3$, $SCF_3$, $SCH_3$, phenoxy, $OC_2H_5$ or $N(CH_3)_2$; in particular phenyl mono- or polysubstituted with F, $OCH_3$, $CH_3$ or phenoxy.

Particularly preferred are tetrahydroimidazopyridine derivatives wherein $R^3$ denotes

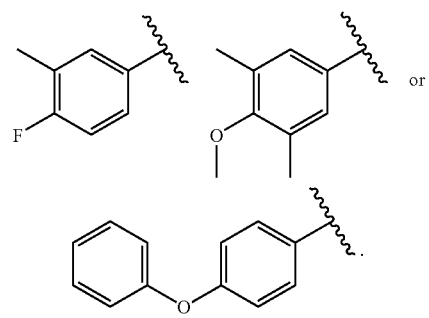

Most preferred are tetrahydroimidazopyridine compounds selected from the group consisting of:

1  (4-Benzylpiperidin-1-yl)(6-phenyl-5,6,7,8-tetrahydroimidazo[1,2-a]pyridin-2-yl)methanone;
2  N-Benzyl-N-phenethyl-6-phenyl-5,6,7,8-tetrahydroimidazo[1,2-a]pyridine-2-carboxamide;
3  (6-Phenyl-5,6,7,8-tetrahydroimidazo[1,2-a]pyridin-2-yl)(1,3,3-trimethyl-6-azabicyclo[3.2.1]octan-6-yl)methanone;
4  (6-(3-Fluorophenyl)-5,6,7,8-tetrahydroimidazo[1,2-a]pyridin-2-yl)(1,3,3-trimethyl-6-azabicyclo[3.2.1]octan-6-yl)methanone;
5  N-Benzyl-6-(4-methoxy-3,5-dimethylphenyl)-5,6,7,8-tetrahydroimidazo[1,2-a]pyridine-2-carboxamide;
6  (4-(2-Fluorophenyl)piperazin-1-yl)(6-(4-methoxy-3,5-dimethylphenyl)-5,6,7,8-tetrahydroimidazo[1,2-a]pyridin-2-yl)methanone;
7  (6-(5-Fluoro-2-methoxyphenyl)-5,6,7,8-tetrahydroimidazo[1,2-a]pyridin-2-yl)(4-(3-(trifluoromethyl)phenyl)piperazin-1-yl)methanone;
8  (4-Benzylpiperidin-1-yl)(6-(5-fluoro-2-methoxyphenyl)-5,6,7,8-tetrahydroimidazo[1,2-a]pyridin-2-yl)methanone;
9  (6-(5-Fluoro-2-methoxyphenyl)-5,6,7,8-tetrahydroimidazo[1,2-a]pyridin-2-yl)(1,3,3-trimethyl-6-azabicyclo[3.2.1]octan-6-yl)methanone;
10  (6-(4-Methoxy-3,5-dimethylphenyl)-5,6,7,8-tetrahydroimidazo[1,2-a]pyridin-2-yl)(4-(2-methoxyphenyl)piperazin-1-yl)methanone;
11  (4-Benzylpiperidin-1-yl)(6-(4-ethylphenyl)-5,6,7,8-tetrahydroimidazo[1,2-a]pyridin-2-yl)methanone;
12  (6-(2,5-Dimethoxyphenyl)-5,6,7,8-tetrahydroimidazo[1,2-a]pyridin-2-yl)(1,3,3-trimethyl-6-azabicyclo[3.2.1]octan-6-yl)methanone;
13  (6-(4-Fluoro-3-methylphenyl)-5,6,7,8-tetrahydroimidazo[1,2-a]pyridin-2-yl)(4-(2-fluorophenyl)piperazin-1-yl)methanone;
14  6-(4-Fluoro-3-methylphenyl)-N-(1-phenylethyl)-5,6,7,8-tetrahydroimidazo[1,2-a]pyridine-2-carboxamide;
15  6-(4-Methoxy-3,5-dimethylphenyl)-N-pentyl-5,6,7,8-tetrahydroimidazo[1,2-a]pyridine-2-carboxamide;
16  N-Hexyl-6-(4-methoxy-3,5-dimethylphenyl)-5,6,7,8-tetrahydroimidazo[1,2-a]pyridine-2-carboxamide;
17  6-(4-Methoxy-3,5-dimethylphenyl)-N-(3-(trifluoromethyl)benzyl)-5,6,7,8-tetrahydroimidazo[1,2-a]pyridine-2-carboxamide;
18  N-sec-Butyl-6-(4-phenoxyphenyl)-5,6,7,8-tetrahydroimidazo[1,2-a]pyridine-2-carboxamide;
19  N-Butyl-6-(4-phenoxyphenyl)-5,6,7,8-tetrahydroimidazo[1,2-a]pyridine-2-carboxamide;
20  Ethyl 1-(6-(4-phenoxyphenyl)-5,6,7,8-tetrahydroimidazo[1,2-a]pyridine-2-carbonyl)piperidine-4-carboxylate;
21  (4-Methylpiperidin-1-yl)(6-(4-phenoxyphenyl)-5,6,7,8-tetrahydroimidazo[1,2-a]pyridin-2-yl)methanone;
22  Ethyl 1-(6-(4-phenoxyphenyl)-5,6,7,8-tetrahydroimidazo[1,2-a]pyridine-2-carbonyl)piperidine-3-carboxylate;
23  1-(4-(6-(4-Phenoxyphenyl)-5,6,7,8-tetrahydroimidazo[1,2-a]pyridine-2-carbonyl)piperazin-1-yl)ethanone;
24  6-(4-Phenoxyphenyl)-N-(pyridin-3-ylmethyl)-5,6,7,8-tetrahydroimidazo[1,2-a]pyridine-2-carboxamide;
25  (6-(4-Phenoxyphenyl)-5,6,7,8-tetrahydroimidazo[1,2-a]pyridin-2-yl)(pyrrolidin-1-yl)methanone;
26  N-Cyclopropyl-6-(4-phenoxyphenyl)-5,6,7,8-tetrahydroimidazo[1,2-a]pyridine-2-carboxamide;
27  N-(3,4-Dimethoxyphenethyl)-6-(4-phenoxyphenyl)-5,6,7,8-tetrahydroimidazo[1,2-a]pyridine-2-carboxamide;
28  N-Pentyl-6-(4-phenoxyphenyl)-5,6,7,8-tetrahydroimidazo[1,2-a]pyridine-2-carboxamide;
29  Pyrrolidin-1-yl(6-m-tolyl-5,6,7,8-tetrahydroimidazo[1,2-a]pyridin-2-yl)methanone;
30  (6-(3,5-Bis(trifluoromethyl)phenyl)-5,6,7,8-tetrahydroimidazo[1,2-a]pyridin-2-yl)(pyrrolidin-1-yl)methanone;
31  Pyrrolidin-1-yl(6-(3-(trifluoromethyl)phenyl)-5,6,7,8-tetrahydroimidazo[1,2-a]pyridin-2-yl)methanone;
32  (4-(2-Fluorophenyl)piperazin-1-yl)(6-(3-(trifluoromethyl)phenyl)-5,6,7,8-tetrahydroimidazo[1,2-a]pyridin-2-yl)methanone;
33  (6-(2,4-Dimethoxyphenyl)-5,6,7,8-tetrahydroimidazo[1,2-a]pyridin-2-yl)(pyrrolidin-1-yl)methanone;
34  Pyrrolidin-1-yl(6-o-tolyl-5,6,7,8-tetrahydroimidazo[1,2-a]pyridin-2-yl)methanone;
35  (6-o-Tolyl-5,6,7,8-tetrahydroimidazo[1,2-a]pyridin-2-yl)(4-(3-(trifluoromethyl)-phenyl)piperazin-1-yl)methanone;
36  (6-(2,5-Difluorophenyl)-5,6,7,8-tetrahydroimidazo[1,2-a]pyridin-2-yl)(pyrrolidin-1-yl)methanone;
37  (6-(4-Ethylphenyl)-5,6,7,8-tetrahydroimidazo[1,2-a]pyridin-2-yl)(pyrrolidin-1-yl)methanone;
38  (6-(4-Fluorophenyl)-5,6,7,8-tetrahydroimidazo[1,2-a]pyridin-2-yl)(1,3,3-trimethyl-6-azabicyclo[3.2.1]octan-6-yl)methanone;
39  6-(4-Methoxyphenyl)-N-(3-(trifluoromethyl)benzyl)-5,6,7,8-tetrahydroimidazo[1,2-a]pyridine-2-carboxamide;
40  6-(4-Ethylphenyl)-N-phenethyl-5,6,7,8-tetrahydroimidazo[1,2-a]pyridine-2-carboxamide;
41  (4-Benzylpiperidin-1-yl)(6-(4-fluorophenyl)-5,6,7,8-tetrahydroimidazo[1,2-a]pyridin-2-yl)methanone;
42  N-(Benzo[d][1,3]dioxol-5-ylmethyl)-6-(3,5-bis(trifluoromethyl)phenyl)-5,6,7,8-tetrahydroimidazo[1,2-a]pyridine-2-carboxamide;
43  N-Benzyl-6-(3,5-bis(trifluoromethyl)phenyl)-5,6,7,8-tetrahydroimidazo[1,2-a]pyridine-2-carboxamide;
44  (6-(4-Methoxy-3,5-dimethylphenyl)-5,6,7,8-tetrahydroimidazo[1,2-a]pyridin-2-yl)(4-(4-methoxyphenyl)piperazin-1-yl)methanone;
45  (4-(2-Ethoxyphenyl)piperazin-1-yl)(6-m-tolyl-5,6,7,8-tetrahydroimidazo[1,2-a]pyridin-2-yl)methanone;
46  (6-(2,4-Dimethoxyphenyl)-5,6,7,8-tetrahydroimidazo[1,2-a]pyridin-2-yl)(4-(3-(trifluoromethyl)phenyl)piperazin-1-yl)methanone;
47  (6-(4-Fluorophenyl)-5,6,7,8-tetrahydroimidazo[1,2-a]pyridin-2-yl)(4-(3-(trifluoromethyl)phenyl)piperazin-1-yl)methanone;
48  (6-(3-Fluorophenyl)-5,6,7,8-tetrahydroimidazo[1,2-a]pyridin-2-yl)(4-(3-(trifluoromethyl)phenyl)piperazin-1-yl)methanone;
49  N-(4-Fluorobenzyl)-6-(4-methoxy-3,5-dimethylphenyl)-5,6,7,8-tetrahydroimidazo-[1,2-a]pyridine-2-carboxamide;
50  (4-Benzylpiperidin-1-yl)(6-(3-methoxyphenyl)-5,6,7,8-tetrahydroimidazo[1,2-a]pyridin-2-yl)methanone;
51  6-(3-Fluorophenyl)-N-(4-phenylbutan-2-yl)-5,6,7,8-tetrahydroimidazo[1,2-a]pyridine-2-carboxamide;
52  6-(4-Ethylphenyl)-N-(4-phenylbutan-2-yl)-5,6,7,8-tetrahydroimidazo[1,2-a]pyridine-2-carboxamide;
53  (6-Phenyl-5,6,7,8-tetrahydroimidazo[1,2-a]pyridin-2-yl)(4-(3-(trifluoromethyl)phenyl)piperazin-1-yl)methanone;
54  (6-(4-Methoxy-3,5-dimethylphenyl)-5,6,7,8-tetrahydroimidazo[1,2-a]pyridin-2-yl)(4-(3-(trifluoromethyl)phenyl)piperazin-1-yl)methanone;
55  (4-Benzylpiperidin-1-yl)(6-(4-methoxy-3,5-dimethylphenyl)-5,6,7,8-tetrahydroimidazo[1,2-a]pyridin-2-yl)methanone;

56 (6-(4-Methoxy-3,5-dimethylphenyl)-5,6,7,8-tetrahydroimidazo[1,2-a]pyridin-2-yl)(1,3,3-trimethyl-6-azabicyclo[3.2.1]octan-6-yl)methanone;
57 4-Benzylpiperidin-1-yl)(6-(4-fluoro-3-methylphenyl)-5,6,7,8-tetrahydroimidazo-[1,2-a]pyridin-2-yl)methanone;
58 (6-(4-Fluoro-3-methylphenyl)-5,6,7,8-tetrahydroimidazo[1,2-a]pyridin-2-yl)(4-(3-(trifluoromethyl)phenyl)piperazin-1-yl)methanone;
59 (4-Benzhydrylpiperazin-1-yl)(6-(4-methoxy-3,5-dimethylphenyl)-5,6,7,8-tetrahydroimidazo[1,2-a]pyridin-2-yl)methanone;
60 6-(3-Methoxyphenyl)-N-(4-phenylbutan-2-yl)-5,6,7,8-tetrahydroimidazo[1,2-a]pyridine-2-carboxamide;
61 (4-Benzylpiperidin-1-yl)(6-(3-fluorophenyl)-5,6,7,8-tetrahydroimidazo[1,2-a]pyridin-2-yl)methanone;
62 (6-(4-Fluoro-3-methylphenyl)-5,6,7,8-tetrahydroimidazo[1,2-a]pyridin-2-yl)(4-(4-(trifluoromethyl)phenyl)piperazin-1-yl)methanone;
63 (6-(4-Fluoro-3-methylphenyl)-5,6,7,8-tetrahydroimidazo[1,2-a]pyridin-2-yl)(4-(4-fluorophenyl)piperazin-1-yl)methanone;
64 (6-(4-Fluoro-3-methylphenyl)-5,6,7,8-tetrahydroimidazo[1,2-a]pyridin-2-yl)(4-(4-methylphenyl)piperazin-1-yl)methanone;
65 (6-(4-Fluoro-3-methylphenyl)-5,6,7,8-tetrahydroimidazo[1,2-a]pyridin-2-yl)(4-(3-methylphenyl)piperazin-1-yl)methanone;
66 (4-Butylpiperazin-1-yl)(6-(4-fluoro-methylphenyl)-5,6,7,8-tetrahydroimidazo[1,2-a]pyridin-2-yl)methanone;
67 (4-Benzhydrylpiperidin-1-yl)(6-(4-fluoro-3-methylphenyl)-5,6,7,8-tetrahydro-imidazo[1,2-a]pyridin-2-yl)methanone;
68 N-(Cyclohexylmethyl)-6-(4-fluoro-3-methylphenyl)-5,6,7,8-tetrahydroimidazo[1,2-a]pyridine-2-carboxamide;
69 (6-(4-Methoxyphenyl)-5,6,7,8-tetrahydroimidazo[1,2-a]pyridin-2-yl)(4-(3-(trifluoromethyl)phenyl)piperazin-1-yl)methanone;
70 (4-Benzylpiperidin-1-yl)(6-m-tolyl-5,6,7,8-tetrahydroimidazo[1,2-a]pyridin-2-yl)methanone;
71 (6-(3-Methoxyphenyl)-5,6,7,8-tetrahydroimidazo[1,2-a]pyridin-2-yl)(4-(3-(trifluoromethyl)phenyl)piperazin-1-yl)methanone;
72 6-(4-Fluoro-3-methylphenyl)-N-(4-phenylbutan-2-yl)-5,6,7,8-tetrahydroimidazo-[1,2-a]pyridine-2-carboxamide;
73 4-Benzylpiperidin-1-yl)(6-p-tolyl-5,6,7,8-tetrahydroimidazo[1,2-a]pyridin-2-yl)methanone;
74 (6-p-Tolyl-5,6,7,8-tetrahydroimidazo[1,2-a]pyridin-2-yl)(4-(3-(trifluoromethyl)-phenyl)piperazin-1-yl)methanone;
75 (6-m-Tolyl-5,6,7,8-tetrahydroimidazo[1,2-a]pyridin-2-yl)(4-(3-(trifluoromethyl)-phenyl)piperazin-1-yl)methanone;
76 (4-Benzylpiperidin-1-yl)(6-(4-methoxyphenyl)-5,6,7,8-tetrahydroimidazo[1,2-a]pyridin-2-yl)methanone;
77 (6-(3,5-Dimethylphenyl)-5,6,7,8-tetrahydroimidazo[1,2-a]pyridin-2-yl)(4-(3-(trifluoromethyl)phenyl)piperazin-1-yl)methanone;
78 N-(1-(3,5-Dimethylphenyl)ethyl)-6-(4-fluoro-3-methylphenyl)-5,6,7,8-tetrahydroimidazo[1,2-a]pyridine-2-carboxamide;
79 6-(3,4-Difluorophenyl)-5,6,7,8-tetrahydroimidazo[1,2-a]pyridin-2-yl)(4-(3-(trifluoromethyl)phenyl)piperazin-1-yl)methanone;
80 (4-Benzylpiperazin-1-yl)(6-(4-fluoro-3-methylphenyl)-5,6,7,8-tetrahydroimidazo-[1,2-a]pyridin-2-yl)methanone;
81 (6-(4-Phenoxyphenyl)-5,6,7,8-tetrahydroimidazo[1,2-a]pyridin-2-yl)(4-(3-(trifluoromethyl)phenyl)piperazin-1-yl)methanone;
82 6-(4-(Benzyloxy)phenyl)-5,6,7,8-tetrahydroimidazo[1,2-a]pyridin-2-yl)(4-(3-(trifluoromethyl)phenyl)piperazin-1-yl)methanone;
83 (6-(4-Fluoro-3-methylphenyl)-5,6,7,8-tetrahydroimidazo[1,2-a]pyridin-2-yl)(4-(3-fluorophenyl)piperazin-1-yl)methanone;
84 (6-(4-Fluoro-3-methylphenyl)-5,6,7,8-tetrahydroimidazo[1,2-a]pyridin-2-yl)(1,3,3-trimethyl-6-azabicyclo[3.2.1]octan-6-yl)methanone;
85 (6-(4-Fluoro-3-methylphenyl)-5,6,7,8-tetrahydroimidazo[1,2-a]pyridin-2-yl)(4-(3-(trifluoromethyl)phenyl)piperidin-1-yl)methanone;
86 6-(4-Fluoro-3-methylphenyl)-N-(4-(3-(trifluoromethyl)phenyl)butan-2-yl)-5,6,7,8-tetrahydroimidazo[1,2-a]pyridine-2-carboxamide;
87 6-(4-Fluoro-3-methylphenyl)-N-methyl-N-(4-(3-(trifluoromethyl)phenyl)butan-2-yl)-5,6,7,8-tetrahydroimidazo[1,2-a]pyridine-2-carboxamide; and
88 N-(2-Cyclohexylethyl)-6-(4-fluoro-3-methylphenyl)-5,6,7,8-tetrahydroimidazo[1,2-a]pyridine-2-carboxamide.

The substituted tetrahydroimidazopyridine compounds according to the invention and the corresponding acids, bases, salts and solvates are suitable as pharmaceutical active ingredients in medicinal products. The present invention therefore also provides a pharmaceutical composition containing at least one substituted tetrahydroimidazopyridine compound according to the invention having the general formula I, wherein the groups $R^1$ to $R^3$ have the meaning given above, and optionally one or more pharmaceutically compatible auxiliary substances.

These pharmaceutical compositions according to the invention are suitable for influencing KCNQ2/3 channels and exert an agonistic or antagonistic, in particular an agonistic, action.

The pharmaceutical compositions according to the invention are suitable for the treatment of disorders or diseases which are at least partly mediated by KCNQ2/3 channels. The pharmaceutical compositions according to the invention are particularly suitable for the treatment of one or more disorders or disease states selected from the group consisting of pain, preferably pain chosen from the group consisting of acute pain, chronic pain, neuropathic pain, muscular pain and inflammatory pain, migraine; epilepsy, anxiety states and urinary incontinence. The medicinal products according to the invention are particularly preferably suitable for the treatment of pain, most particularly preferably chronic pain, neuropathic pain, inflammatory pain and muscular pain. The compounds according to the invention are further preferably suitable for the treatment of epilepsy.

The present invention also provides the use of at least one substituted tetrahydroimidazopyridine compound according to the invention and optionally one or more pharmaceutically compatible auxiliary substances for the preparation of a medicinal product for the treatment of disorders or diseases which are at least partly mediated by KCNQ2/3 channels.

Preference is given to the use of at least one substituted tetrahydroimidazo-pyridine compound according to the invention and optionally one or more pharmaceutically compatible auxiliary substances for the preparation of a medicinal product for the treatment of pain, preferably pain chosen from the group consisting of acute pain, chronic pain, neuropathic pain, muscular pain and inflammatory pain; migraine; epilepsy, anxiety states and urinary incontinence.

Particularly preferred is the use of at least one substituted tetrahydroimidazopyridine compound according to the invention and optionally one or more pharmaceutically compatible auxiliary substances for the preparation of a medicinal product for the treatment of pain, most particularly preferably chronic pain, neuropathic pain, inflammatory pain and muscular pain. Also particularly preferred is the use of at least one substituted tetrahydroimidazopyridine compound according to the invention and optionally one or more pharmaceutically compatible auxiliary substances for the preparation of a medicinal product for the treatment of epilepsy.

The effectiveness against pain can be shown, for example, in the Bennett or Chung model described below. The effectiveness against epilepsy can be demonstrated, for example, in the DBA/2 mouse model (De Sarro et al., Naunyn-Schmiedeberg's Arch. Pharmacol. 2001, 363, 330-336).

The present invention also provides a process for preparing the substituted tetrahydroimidazopyridine compounds according to the invention. The chemicals and reaction components used in the reactions described above are available commercially or can be prepared by methods known to the person skilled in the art.

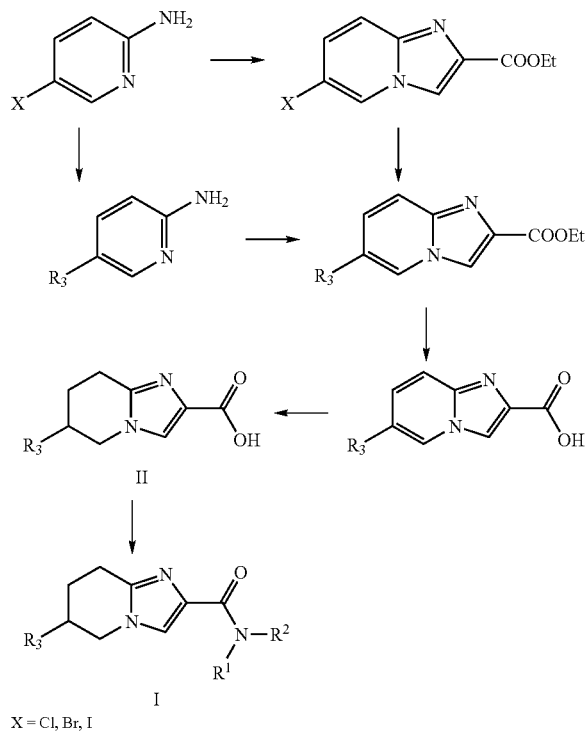

X = Cl, Br, I

Starting from a correspondingly iodine-, bromine- or chlorine-substituted 2-aminopyridine, cyclisation is performed by reaction with 3-bromo-2-oxopropionic acid ethyl ester in an organic solvent, for example ethanol, methanol, THF, 1,2-dimethoxyethane, acetone, water or chloroform, at temperatures of between 0° C. and 80° C. for a reaction time of 2 to 48 h. Alternatively, the cyclisation reaction can also take place starting from the primarily formed 2-aminopyridinium bromide by heating in methanol.

The subsequent Suzuki reaction is performed by reacting the corresponding iodine-, bromine- or chlorine-substituted imidazole with phenylboric acids or phenylboric acid esters in solvents such as methanol, ethanol, 1-propanol, ethylene glycol, water, 1,2-dimethoxyethane, THF, dioxane, acetonitrile, DMF, benzene, toluene or xylene, which can also be present as blends, using a catalyst, a base and optionally an additive.

Catalysts which can be used are inter alia $Pd(PPh_3)_4$, $Pd(dba)_2$, $PdCl_2(dppf)_2$, $Pd(P(o\text{-}tolyl)_3)_4$, $PdCl_2(PPh_3)_2$, $PdCl_2(P(Cy)_3)_2$, $Pd(OAc)_2(P(o\text{-}tolyl)_3)_2$. In addition, a mixture of $Pd(OAc)_2/PPh_3$, Pd on activated carbon/$PPh_3$ or $(NH_4)_2$ $PdCl_4$ can be used as catalyst. Tri-tert-butyl phosphine is suitable as a further ligand. Both organic and inorganic bases can be used as bases. TEA or sodium tert-butylate, for example, are suitable as organic bases. Sodium carbonate, sodium hydrogen carbonate, potassium carbonate, caesium carbonate or silver carbonate, barium hydroxide, sodium hydroxide or potassium hydroxide or potassium phosphate, for example, are suitable as inorganic bases. EDTA, tetrabutylammonium bromide, lithium chloride, potassium fluoride or methyl cyclohexane, for example, can be used as additives. The reaction temperature is between room temperature and 80° C., with a reaction time of 1.5 to 72 hours. The reaction can also be performed in the microwave.

Another reaction pathway starts from iodine-, bromine- or chlorine-substituted 2-aminopyridines, which are first converted to the phenyl-substituted aminopyridines in a Suzuki reaction. The Suzuki reaction is performed by reacting the corresponding iodine-, bromine- or chlorine-substituted 2-aminopyridine with boric acids or boric acid esters in solvents, for example methanol, ethanol, 1-propanol, ethylene glycol, water, 1,2-dimethoxyethane, THF, dioxane, acetonitrile, DMF, benzene, toluene or xylene, which can also be present as blends, using a catalyst, a base and optionally an additive.

Catalysts which can be used are inter alia $Pd(PPh_3)_4$, $Pd(dba)_2$, $PdCl_2(dppf)_2$, $Pd(P(o\text{-}tolyl)_3)_4$, $PdCl_2(PPh_3)_2$, $PdCl_2(P(Cy)_3)_2$, $Pd(OAc)_2(P(o\text{-}tolyl)_3)_2$. In addition, a mixture of $Pd(OAc)_2/PPh_3$, Pd on activated carbon/$PPh_3$ or $(NH_4)_2$ $PdCl_4$ can be used as catalyst. Tri-tert-butyl phosphine is suitable as a further ligand.

Either organic or inorganic bases can be used as bases. TEA or sodium tert-butylate, for example, are suitable as organic bases. Sodium carbonate, sodium hydrogen carbonate, potassium carbonate, caesium carbonate or silver carbonate, barium hydroxide, sodium hydroxide or potassium hydroxide or potassium phosphate, for example, are suitable as inorganic bases. EDTA, tetrabutylammonium bromide, lithium chloride, potassium fluoride or methyl cyclohexane, for example, can be used as additives. The reaction temperature is between room temperature and 80° C., with a reaction time of 1.5 to 72 hours. The reaction can also be performed in the microwave.

Cyclization can be carried out by reacting the phenyl-substituted aminopyridine with 3-bromo-2-oxopropionic acid ethyl ester in an organic solvent, for example ethanol, methanol, THF, 1,2-dimethoxyethane, acetone, water or chloroform, at temperatures of between 0° C. and 80° C. for a reaction time of 2 to 48 h. Alternatively, the cyclisation reaction can also take place starting from the primarily formed 2-aminopyridinium bromide by heating in methanol.

The subsequent ester cleavage can be performed using organic acids, for example trifluoroacetic acid, or aqueous inorganic acids, for example hydrochloric acid, or using aqueous inorganic bases, for example lithium hydroxide, potassium hydroxide, sodium hydroxide, sodium carbonate, sodium hydrogen carbonate, potassium carbonate, in organic solvents, for example methanol, dioxane, dichloromethane, THF, diethyl ether or in these solvents as blends.

The subsequent hydrogenation can be performed with Pd on activated carbon, Raney nickel, platinum or $PtO_2$. Suitable solvents are, for example, ethanol, methanol, water, acetic acid, propionic acid, DCM, cyclohexane, methanolic KOH or blends of these solvents. TFA, for example, can be used as an additive. The reaction can be performed under normal pressure or elevated pressure. The reaction time can be between 1.5 and 72 hours.

The subsequent acylation can be performed both with acid chlorides or bromides, which can also be produced from carboxylic acids having the general formula II, and with carboxylic acids having the general formula II.

The carboxylic acids corresponding to formula II that are obtained can be converted into acid chlorides or bromides by methods known to persons skilled in the art. The carboxylic acid chlorides or bromides that are obtained can be reacted in solvents, for example DCM, benzene, toluene, THF, DMF, acetonitrile, pyridine, dioxane, water or 1-methylpyrrolidin-2-one or blends of these solvents, using bases, for example pyridine, DIEA, TEA, N-methylmorpholine or sodium hydrogen carbonate, optionally with addition of a coupling reagent, for example DCC, with primary or secondary amines. The reaction temperature can be varied between −20° C. and +110° C. The reaction times can be between 0.5 h and 24 hours.

The reaction of carboxylic acids having the general formula II with primary or secondary amines can be performed using bases and optionally coupling reagents in solvents, for example methanol, DMF or DCM. Sodium methanolate, TEA, DIEA or N-methylmorpholine, for example, can be used as bases. EDCI, HOBt, DCC, CDI, HBTU, DMAP or pentafluorophenyl diphenyl phosphinate, for example, are suitable as coupling reagents. The reaction time can vary between 1 and 3 days.

EXAMPLES

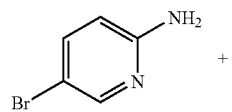

+

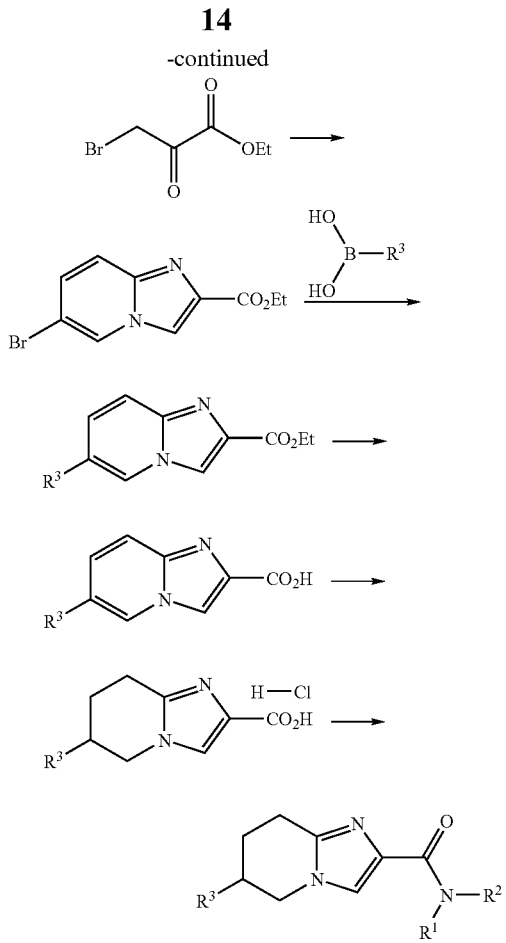

The following tetrahydroimidazopyridines were used for the syntheses:

| | |
|---|---|
| S1 | 6-Phenyl-5,6,7,8-tetrahydroimidazo[1,2-a]pyridine-2-carboxylic acid |
| S2 | 6-(4-Methoxy-3,5-dimethylphenyl)-5,6,7,8-tetrahydroimidazo[1,2-a]pyridine-2-carboxylic acid |
| S3 | 6-(4-Fluoro-3-methylphenyl)-5,6,7,8-tetrahydroimidazo[1,2-a]pyridine-2-carboxylic acid |
| S4 | 6-(3-Methoxyphenyl)-5,6,7,8-tetrahydroimidazo[1,2-a]pyridine-2-carboxylic acid |
| S5 | 6-(3-Fluorophenyl)-5,6,7,8-tetrahydroimidazo[1,2-a]pyridine-2-carboxylic acid |
| S6 | 6-(4-Methoxyphenyl)-5,6,7,8-tetrahydroimidazo[1,2-a]pyridine-2-carboxylic acid |
| S7 | 6-(5-Fluoro-2-methoxyphenyl)-5,6,7,8-tetrahydroimidazo[1,2-a]pyridine-2-carboxylic acid |
| S8 | 6-(3,5-Dimethoxyphenyl)-5,6,7,8-tetrahydroimidazo[1,2-a]pyridine-2-carboxylic acid |
| S9 | 6-(4-Ethylphenyl)-5,6,7,8-tetrahydroimidazo[1,2-a]pyridine-2-carboxylic acid |
| S10 | 6-(4-Fluorophenyl)-5,6,7,8-tetrahydroimidazo[1,2-a]pyridine-2-carboxylic acid |
| S11 | 6-(4-Phenoxyphenyl)-5,6,7,8-tetrahydroimidazo[1,2-a]pyridine-2-carboxylic acid |
| S12 | 6-(3-Methylphenyl)-5,6,7,8-tetrahydroimidazo[1,2-a]pyridine-2-carboxylic acid |
| S13 | 6-(2,5-Difluorophenyl)-5,6,7,8-tetrahydroimidazo[1,2-a]pyridine-2-carboxylic acid |
| S14 | 6-(3,5-Bis(trifluoromethyl)phenyl)-5,6,7,8-tetrahydroimidazo[1,2-a]pyridine-2-carboxylic acid |
| S15 | 6-(3-(Trifluoromethyl)phenyl)-5,6,7,8-tetrahydroimidazo[1,2-a]pyridine-2-carboxylic acid |
| S16 | 6-2,4-Dimethoxyphenyl)-5,6,7,8-tetrahydroimidazo[1,2-a]pyridine-2-carboxylic acid |
| S17 | 6-(2-Methylphenyl)-5,6,7,8-tetrahydroimidazo[1,2-a]pyridine-2-carboxylic acid |
| S18 | 6-(4-Methylphenyl)-5,6,7,8-tetrahydroimidazo[1,2-a]pyridine-2-carboxylic acid |
| S19 | 6-(3,4-Difluorophenyl)-5,6,7,8-tetrahydroimidazo[1,2-a]pyridine-2-carboxylic acid |
| S20 | 6-(3,5-Dimethylphenyl)-5,6,7,8-tetrahydroimidazo[1,2-a]pyridine-2-carboxylic acid |
| S21 | 6-(4-(Benzyloxy)phenyl)-5,6,7,8-tetrahydroimidazo[1,2-a]pyridine-2-carboxylic acid |

-continued

| Starting product for structural unit | Name | Supplier |
|---|---|---|
| S1 | Phenylboric acid | Acros |
| S2 | 3,5-Dimethyl-4-methoxyphenylboric acid | Aldrich |
| S3 | 4-Fluoro-3-methylphenylboric acid | Aldrich |
| S4 | 3-Methoxyphenylboric acid | Acros |
| S5 | 3-Fluorophenylboric acid | Acros |
| S6 | 4-Methoxyphenylboric acid | Acros |
| S7 | 5-Fluoro-2-methoxyphenylboric acid | Aldrich |
| S8 | 2,5-Dimethoxyphenylboric acid | Acros |
| S9 | 4-Ethylphenylboric acid | Acros |
| S10 | 4-Fluorophenylboric acid | Acros |
| S11 | 4-Phenoxyphenylboric acid | Acros |
| S12 | 3-Tolylboric acid | Acros |
| S13 | 2,5-Difluorophenylboric acid | Acros |
| S14 | 3,5-Bis-(trifluoromethyl)phenylboric acid | Acros |
| S15 | 3-Trifluoromethylphenylboric acid | Acros |
| S16 | 2,4-Dimethoxyphenylboric acid | Acros |
| S17 | 2-Tolylboric acid | Acros |
| S18 | 4-Tolylboric acid | Acros |
| S19 | 3,4-Difluorophenylboric acid | Acros |
| S20 | 3,5-Dimethylphenylboric acid | Aldrich |
| S21 | 4-(Benzyloxy)phenylboric acid | Interchim |

6-Bromoimidazo[1,2-a]pyridine-2-carboxylic Acid Ethyl Ester

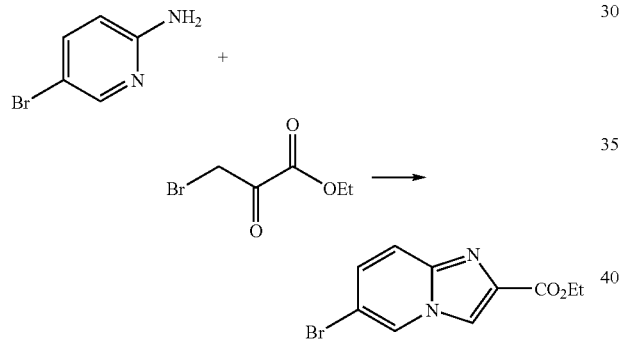

Ethylbromopyruvate (62.0 g; 318 mmol; 40.0 ml) was added to a solution of 5-bromo-2-aminopyridine (50.0 g; 289 mmol) in ethanol (500 ml) through a dropping funnel. The reaction batch was first stirred for 30 min at room temperature and then refluxed for 8 hours while stirring (DC control: DCE-ethanol 5:1). The solvent was removed under vacuum and the residue taken up in DCM. It was washed first with saturated common salt solution and then with saturated sodium hydrogen carbonate solution. The organic phase was dried over magnesium sulfate, filtered and concentrated to dryness. The residue was recrystallized from dry diethyl ether. Yield: 41 g (53%)

6-Phenyl-5,6,7,8-tetrahydroimidazo[1,2-a]pyridine-2-carboxylic Acid S1

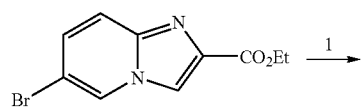

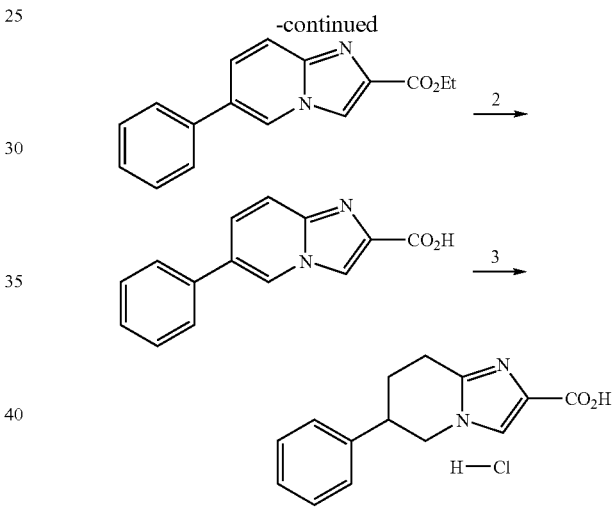

Stage 1. Phenylboric acid (2.13 g; 17.5 mmol) followed by KF solution (2M in water, 15 ml) and finally Pd(PPh$_3$)$_4$ (607 mg; 0.5 mmol; 3 mol %) were added under a nitrogen atmosphere to a solution of 6-bromoimidazo[1,2-a]pyridine-2-carboxylic acid ethyl ester (4.71 g; 17.5 mmol) in acetonitrile (30 ml) in a Milestone 100 ml high-pressure vessel. The reaction vessel was rinsed with nitrogen, closed and irradiated in a microwave at 160° C. for 5 min. (DC control: n-hexane-ethyl acetate 1:1). Two batches of the same size were run in parallel and combined prior to processing. The precipitated product was filtered out and washed with diethyl ether. The black crystalline product was taken up in chloroform and filtered first over silica gel and then over celite. The clear filtrate was concentrated to dryness. Yield: 9.3 g (100%).

Stage 2. The 6-phenylimidazo[1,2-a]pyridine-2-carboxylic acid ethyl ester (9.32 g, 17.5 mmol) was dissolved in ethanol (80 ml) and NaOH solution (20% in water, 7 ml) was added. The reaction batch was refluxed for 8 hours. On completion of the reaction the solvent was removed in a rotary evaporator and the residue taken up in a small amount of water. The solution was carefully adjusted to pH 3-4 with HCl solution (10% in water). The precipitated product was filtered and washed with water and used in the next stage without further purification. Yield: 7.90 g (95%).

Stage 3. Palladium on activated carbon (1.5 g) was added to a solution of 6-phenylimidazo[1,2-a]pyridine-2-carboxylic acid (6.3 g; 26.4 mmol) in a blend of HCl (4% in water, 100 ml) and ethanol (200 ml). The mixture was poured into an autoclave (stainless steel), the autoclave was closed and rinsed a few times with nitrogen. The autoclave was filled with hydrogen (8 bar) and the reaction batch stirred over the weekend at room temperature. The catalyst was filtered out over celite and the solvent drawn off in a rotary evaporator at room temperature. The product was crystallized out of acetonitrile. Yield: 4.1 g (56%).

6-(4-Methoxy-3,5-dimethylphenyl)-5,6,7,8-tetrahydroimidazo[1,2-a]pyridine-2-carboxylic Acid Hydrochloride S2

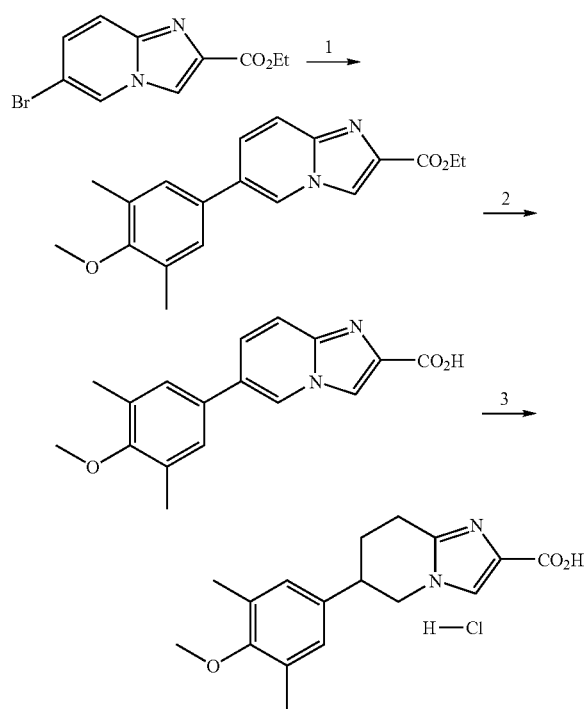

Stage 1. 4-Methoxy-3,5-dimethylphenylboric acid (3.15 g; 17.5 mmol) followed by KF solution (2M in water, 15 ml) and finally Pd(PPh$_3$)$_4$ (607 mg; 0.525 mmol; 3 mol %) were added under a nitrogen atmosphere to a solution of 6-bromoimidazo[1,2-a]pyridine-2-carboxylic acid ethyl ester (4.71 g; 17.5 mmol) in acetonitrile (30 ml) in a Milestone 100 ml high-pressure vessel. The reaction vessel was rinsed with nitrogen, closed and irradiated in a microwave at 160° C. for 5 min. (DC control: n-hexane-ethyl acetate 1:1). Four batches of the same size were run in parallel and combined prior to processing. The precipitated product was filtered out and washed with diethyl ether. The black crystalline product was taken up in chloroform and filtered over celite. The clear filtrate was concentrated to small volume and used for the next reaction without further purification. Yield: 22.7 g (quantitative).

Stage 2. The 6-(4-methoxy-3,5-dimethylphenyl)-imidazo[1,2-a]pyridine-2-carboxylic acid ethyl ester (22.7 g, 70 mmol) was dissolved in ethanol (300 ml) and NaOH solution (20% in water, 30 ml) was added. The reaction batch was refluxed for 24 hours. On completion of the reaction the solvent was removed in a rotary evaporator and the residue taken up in as small an amount of water as possible. The solution was carefully adjusted to pH 3-4 with HCl solution (10% in water). The precipitated product was filtered and washed with water. Yield: 21.2 (quantitative).

Stage 3. Palladium on activated carbon (1 g) was added to a solution of 6-(4-methoxy-3,5-dimethylphenyl)-imidazo[1,2-a]pyridine-2-carboxylic acid (4.74 g; 16 mmol) in a blend of HCl (4% in water, 70 ml) and ethanol (140 ml). The mixture was poured into an autoclave (stainless steel), the autoclave was closed and rinsed a few times with nitrogen. The autoclave was filled with hydrogen (8 bar) and the reaction batch stirred for 12 h at room temperature. On completion of the reaction the catalyst was filtered out over celite and the solvent drawn off in a rotary evaporator at room temperature. The product was crystallized out of acetonitrile. Yield: 2.3 g (43%).

6-(4-Fluoro-3-methylphenyl)-5,6,7,8-tetrahydroimidazo[1,2-a]pyridine-2-carboxylic Acid S3

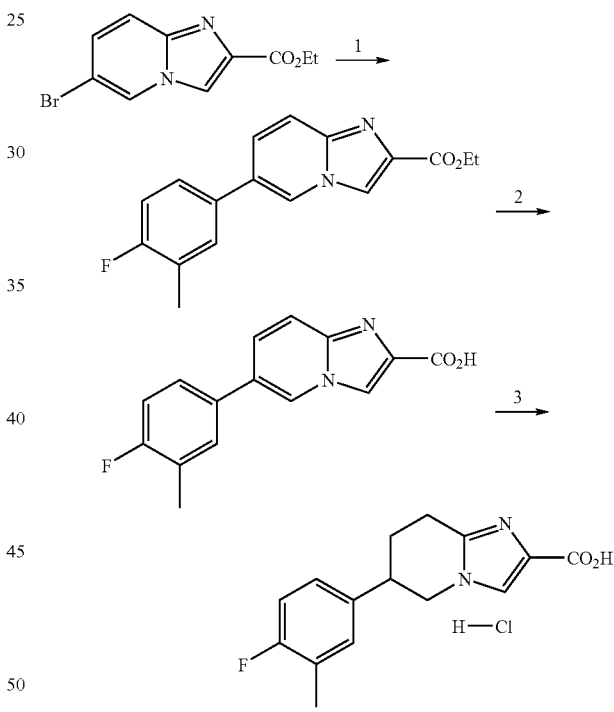

Stage 1. 4-Fluoro-3-methylphenylboric acid (4.62 g; 15 mmol) followed by KF solution (2M in water, 15 ml) and finally Pd(PPh$_3$)$_4$ (520 mg; 0.45 mmol; 3 mol %) were added under a nitrogen atmosphere to a solution of 6-bromoimidazo[1,2-a]pyridine-2-carboxylic acid ethyl ester (4.04 g; 15 mmol) in acetonitrile (30 ml) in a Milestone 100 ml high-pressure vessel. The reaction vessel was rinsed with nitrogen, closed and irradiated in a microwave at 160° C. for 5 min. (DC control: n-hexane-ethyl acetate 1:1). Two batches of the same size were run in parallel and combined prior to processing. The precipitated product was filtered out and washed with diethyl ether. The black crystalline product was taken up in chloroform and filtered over celite. The clear filtrate was concentrated to small volume and crystallized out of diethyl ether. Yield: 4.5 g (50%).

Stage 2. The 6-(4-fluoro-3-methylphenyl)-imidazo[1,2-a]pyridine-2-carboxylic acid ethyl ester (3.0 g, 10.1 mmol) was dissolved in ethanol (50 ml) and NaOH solution (20% in water, 4 ml) was added. The reaction batch was refluxed for 2 hours. On completion of the reaction the solvent was removed in a rotary evaporator and the residue taken up in as small an amount of water as possible. The solution was carefully adjusted to pH 3-4 with HCl solution (10% in water). The precipitated product was filtered and washed with water. The crude product was used in the next stage without further purification. Yield: 1.69 g (62%).

Stage 3. Palladium on activated carbon (350 mg) was added to a solution of 6-(4-fluoro-3-methylphenyl)-imidazo[1,2-a]pyridine-2-carboxylic acid (1.69 g; 6.2 mmol) in a blend of HCl (4% in water, 20 ml) and ethanol (40 ml). The mixture was poured into an autoclave (stainless steel), the autoclave was closed and rinsed a few times with nitrogen. The autoclave was filled with hydrogen (8 bar) and the reaction batch stirred for 20 h at room temperature. The catalyst was filtered out over celite, and the solvent drawn off in a rotary evaporator at room temperature. The product was crystallized out of acetonitrile. As the reaction did not run to completion, the crude product mixture was dissolved again in a blend of HCl (4% in water, 15 ml) and ethanol (30 ml), palladium on activated carbon (260 mg) was added, and the mixture was poured into an autoclave (stainless steel), which was closed and rinsed a few times with nitrogen. The autoclave was filled with hydrogen (8 bar) and the reaction batch stirred for a further 12 hours at room temperature. The catalyst was filtered out over celite and the solvent drawn off in a rotary evaporator at room temperature. The product was crystallized out of acetonitrile. Yield: 609 mg (31%).

6-(3-Methoxyphenyl)-5,6,7,8-tetrahydroimidazo[1,2-a]pyridine-2-carboxylic Acid Hydrochloride S4

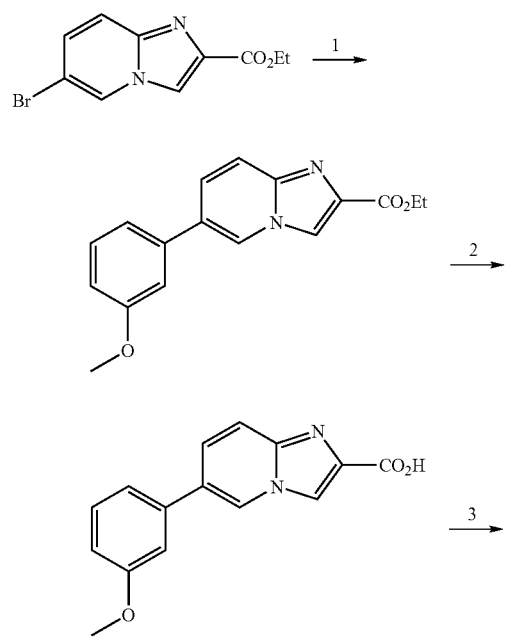

-continued

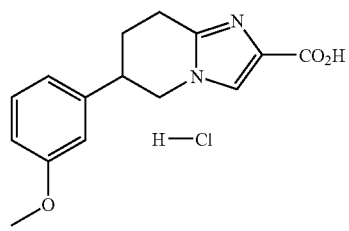

Stage 1. 3-Methoxyphenylboric acid (2.66 g; 17.5 mmol) followed by KF solution (2M in water, 15 ml) and finally Pd(PPh$_3$)$_4$ (606 mg; 0.525 mmol; 3 mol %) were added under a nitrogen atmosphere to a solution of 6-bromoimidazo[1,2-a]pyridine-2-carboxylic acid ethyl ester (4.71 g; 17.5 mmol) in acetonitrile (30 ml) in a Milestone 100 ml high-pressure vessel. The reaction vessel was rinsed with nitrogen, closed and irradiated in a microwave at 160° C. for 5 min. (DC control: n-hexane-ethyl acetate 1:1). Four batches of the same size were run in parallel and combined prior to processing. The precipitated product was filtered out and washed with diethyl ether. The black crystalline product was taken up in chloroform and filtered over celite. The clear filtrate was concentrated to small volume and crystallized out of diethyl ether. Yield: 15.48 g (75%).

Stage 2. The 6-(3-methoxyphenyl)-imidazo[1,2-a]pyridine-2-carboxylic acid ethyl ester (15.48 g, 52 mmol) was dissolved in ethanol (150 ml) and NaOH solution (20% in water, 10 ml) was added. The reaction batch was refluxed for 8 hours. On completion of the reaction the solvent was removed in a rotary evaporator and the residue taken up in as small an amount of water as possible. The solution was carefully adjusted to pH 3-4 with HCl solution (10% in water). The precipitated product was filtered and washed with water. Yield: 7.93 g (57%).

Stage 3. Palladium on activated carbon (300 mg) was added to a solution of 6-(3-methoxyphenyl)-imidazo[1,2-a]pyridine-2-carboxylic acid (1.38 g; 5.15 mmol) in a blend of HCl (4% in water, 60 ml) and ethanol (90 ml). The mixture was poured into an autoclave (stainless steel), the autoclave was closed and rinsed a few times with nitrogen. The autoclave was filled with hydrogen (8 bar) and the reaction batch stirred for 5 h at room temperature. On completion of the reaction the catalyst was filtered out over celite and the solvent drawn off in a rotary evaporator at room temperature. The product was crystallized out of acetonitrile.

Yield: 1.30 g (82%)

Synthesis of Structural Units S5, S6, S10, S12, S18-S20

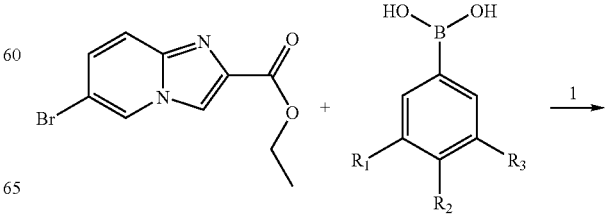

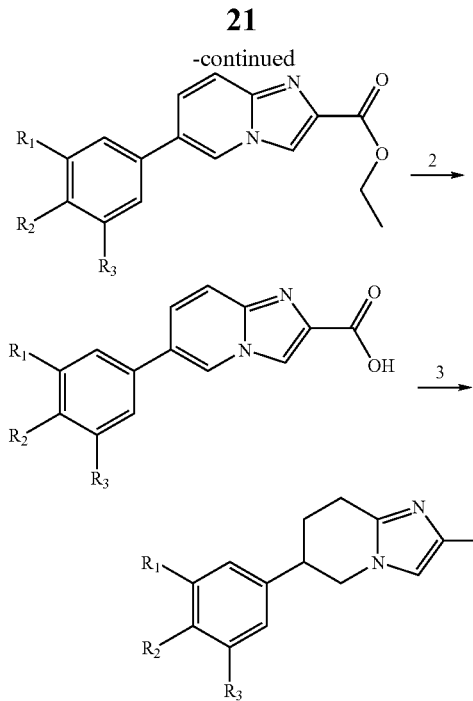

Stage 1. The corresponding boric acid (2.04 mmol) followed by $K_2CO_3$ (4.65 mmol), water (1.5 ml) and ethanol (3.5 ml) were added to a solution of 6-bromoimidazo[1,2-a]pyridine-2-carboxylic acid ethyl ester (1.86 mmol) in toluene (7 ml). Argon was passed through the reaction solution for 15 min. Finally Pd(PPh$_3$)$_4$ (0.093 mmol) was added and the mixture was gassed with argon for a further 15 min. The mixture was then refluxed for 15 hours. On completion of the reaction (DC control) the reaction batch was diluted with ethyl acetate and washed first with water and then with saturated sodium chloride solution. The organic phase was dried over sodium sulfate and the solvent was drawn off completely. The products were crystallized out of a mixture of 25% diethyl ether in hexane, filtered and dried.

Stage 2. The Suzuki product was dissolved in ethanol and NaOH solution (20% in water) was added. The reaction batch was refluxed for 2 hours. On completion of the reaction the solvent was removed in a rotary evaporator and the residue taken up in as small an amount of water as possible. The solution was carefully adjusted to pH 3-4 with HCl solution (10% in water). The precipitated product was filtered and washed with water. The product was taken up in toluene, concentrated to small volume and then dried.

Stage 3. Palladium on activated carbon (1.53 g) was added to a solution of the free acid in a blend of HCl (3% in water, 175 ml) and ethanol (88 ml). The mixture was poured into an autoclave (stainless steel), the autoclave was closed and rinsed a few times with nitrogen. The autoclave was filled with hydrogen (8 bar) and the reaction batch stirred for 8 h at room temperature. On completion of the reaction the catalyst was filtered out over celite and the solvent drawn off in a rotary evaporator at 45° C. The product was crystallized out of methanol diethyl ether.

| | $R_1$ | $R_2$ | $R_3$ | Yield (over 3 stages) (%) |
|---|---|---|---|---|
| S5 | F | H | H | 25 |
| S6 | H | OCH$_3$ | H | 18 |
| S10 | H | F | H | 10 |
| S12 | CH$_3$ | H | H | 36 |
| S18 | H | CH$_3$ | H | 21 |
| S19 | F | F | H | 33 |
| S20 | CH$_3$ | H | CH$_3$ | 61 |

The following commercially available amines were used for the syntheses:

| No. | Name | Supplier |
|---|---|---|
| A01 | 1-(2-Methoxyphenyl)piperazine | Aldrich |
| A02 | Benzylamine | Aldrich |
| A03 | 2-Phenylethylamine | Aldrich |
| A04 | 3-Picolylamine | Aldrich |
| A05 | 4-Benzylpiperidine | Aldrich |
| A06 | Cyclopropylamine | Aldrich |
| A07 | Ethyl piperidine-4-carboxylate | Aldrich |
| A08 | N-Benzyl-2-phenethylamine | Aldrich |
| A09 | 2-(3,4-Dimethoxyphenyl)ethanamine | Aldrich |
| A10 | Ethyl piperidine-3-carboxylate | Aldrich |
| A11 | 1-(Piperazin-1-yl)ethanone | Aldrich |
| A12 | Pyrrolidine | Aldrich |
| A13 | 4-(2-Fluorophenyl)piperazine | Aldrich |
| A14 | Benzo[d][1,3]dioxol-5-ylmethanamine | Aldrich |
| A15 | Butylamine | Aldrich |
| A16 | 4-Fluorobenzylamine | Aldrich |
| A17 | 1,3,3-Trimethyl-6-azabicyclo[3.2.1]octane | Acros |
| A18 | Amylamine | Aldrich |
| A19 | 4-(3-Trifluoromethylphenyl)piperazine | Aldrich |
| A20 | Hexylamine | Aldrich |
| A21 | 4-Methylpiperidine | Aldrich |
| A22 | 4-Phenylbutyl-2-amine | Aldrich |
| A23 | (3-(Trifluoromethyl)phenyl)methanamine | Aldrich |
| A24 | sec-Butylamine | Aldrich |
| A25 | 4-(4-Methoxyphenyl)piperazine | Aldrich |
| A26 | a-Methylbenzylamine | Aldrich |
| A27 | 4-(2-Ethoxyphenyl)piperazine | Aldrich |
| A28 | 1-Benzhydrylpiperazine | Acros |
| A29 | 1-(4-(Trifluoromethyl)phenyl)piperazine | Acros |
| A30 | 4-(4-Fluorophenyl)piperazine | Acros |
| A31 | 4-(4-Methylphenyl)piperazine | Acros |
| A32 | 4-(3-Methylphenyl)piperazine | Acros |
| A33 | Cyclohexylmethanamine | Lancaster |
| A34 | 1-Butylpiperazine | Fluka |
| A36 | 1-Benzylpiperazine | ACBBlocks |
| A37 | 1-(3-Fluorophenyl)piperazine | ABCR |
| A38 | 2-Cyclohexylethanamine | Alfa-Aesar |
| A39 | 4-(3-(Trifluoromethyl)phenyl)piperidine | Apollo |

Synthesis of 1-(3,5-dimethylphenyl)ethanamine A35

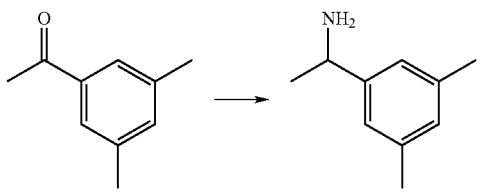

3,5-Dimethylacetophenone (3.0 g, 20.2 mmol) was dissolved in ethanolic NH$_3$ solution (2 M in ethanol, 50 ml), tetrapropylorthotitanate (11 ml, 40.4 ml) was added and the mixture was stirred for 6 h at room temperature. NaBH$_4$ (1.16 g, 30.4 mmol) was then added carefully to the reaction solution and the mixture was stirred overnight at room temperature. The reaction mixture was poured into aqueous ammonia solution and filtered. The solid was washed twice more with ethyl acetate (50 ml). The phases were separated and the aqueous phase was extracted twice more with ethyl acetate. The combined organic phases were washed with HCl solution (2 N, 60 ml), the aqueous phase was adjusted to pH 11 with NaOH solution and extracted three times with ethyl acetate (100 ml). The organic phase was washed with saturated NaCl solution (100 ml), dried over MgSO$_4$ and concentrated to small volume. The resulting crude product was used without further purification. Yield: 43%.

Synthesis of
4-(3-(trifluoromethyl)phenyl)butan-2-amine A40

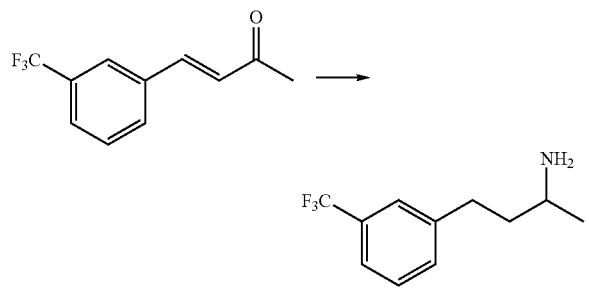

The ketone and liquid ammonia (10 ml/mmol) were poured into the reaction vessel of a hydrogenator and Raney nickel (0.12 g/mmol) was added. The reaction batch was shaken at room temperature for 16 h under hydrogen pressure (50 psi). The reaction mixture was filtered over diatomaceous earth and rewashed three times with DCM. The combined organic phases were dried over Na$_2$SO$_4$ and concentrated to dryness. The crude product was taken up in dioxane saturated with HCl. The solvent was removed in a rotary evaporator and the remaining solid mass treated with diethyl ether. The product was obtained as HCl salt.

Synthesis of N-methyl-4-(3-(trifluoromethyl)phenyl)butan-2-amine A41

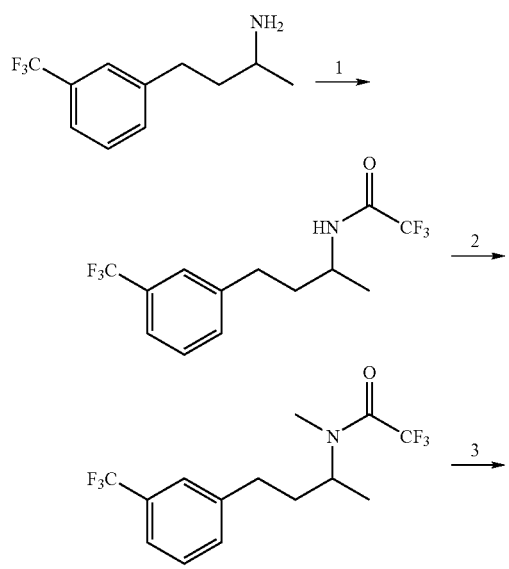

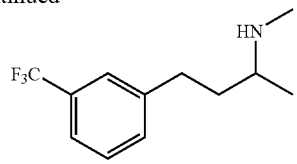

Stage 1. TEA (5 eq) was added to a solution of the amine (1 eq) in DCM at room temperature, followed dropwise by TFAA (2 eq). The reaction batch was stirred for 4 h at room temperature (DC control). The reaction mixture was washed with saturated ammonium chloride solution and saturated sodium chloride solution. The organic phase was dried over Na$_2$SO$_4$ and concentrated to dryness. The resulting crude product was purified by column chromatography (silica gel, 15% ethyl acetate in hexane).
Yield: 58%

Stage 2. KOtBu was added to a solution of the amide (1 eq) in DMF (2 ml/mmol) at room temperature, followed by methyl iodide (5 eq), and the mixture was stirred for 2 h at 0° C. (DC control). The reaction batch was poured onto ice and the product extracted with ethyl acetate. The organic phase was washed with saturated sodium chloride solution, dried over Na$_2$SO$_4$ and concentrated to dryness. The resulting crude product was purified by column chromatography (silica gel, 5% ethyl acetate in hexane). Yield: 76%.

Stage 3. The methylated amide was dissolved in methanol (4 ml/mmol) and 1 N NaOH (4 ml/mmol) was added. The reaction batch was then stirred for 2 h at room temperature (DC control). The methanol was removed in a rotary evaporator and the product was extracted three times with ethyl acetate. The combined organic phases were dried over Na$_2$SO$_4$ and then concentrated to dryness. The resulting crude product was used without further purification. Yield: 78%.

Example Compounds

Automated Synthesis
Preparation of the Stock Solutions:
Solution A (Solution of the Acid Structural Unit in DMA):
The hydrochloride of the acid used was first dried in a vacuum drying oven before use. The corresponding compound was first mixed with 3 molar equivalents of 4-methylmorpholine in DMA at room temperature. Then sufficient solvent was added to produce a 0.15-0.2 molar solution.
Solution B (Solution of TBTU in DMA):
Solution B was produced from TBTU in DMA (0.3 mol/l).
Solution C (Solution of the Amine Structural Unit in DMA):
Solution C was produced from the corresponding amine in DMA (0.5 mol/l).

Solution A (100 µmol, 0.5-0.66 ml) and solution B (120 µmol, 0.4 ml) were poured into standard glass reaction vessels using a Cavro RSP9000 robotic system and reacted for 15 min. Then solution C (120 µmol, 0.24 ml) was added using a Cavro RSP9000 robotic system. The reaction batch was then stirred for 16-20 h at room temperature (DC control). The batches were processed by first removing the solvent under vacuum and then adding chloroform (2.5 ml) to the residue. The solution was then extracted first with water (1 ml), then with NaOH solution (10% in water, 1 ml) and subsequently with water (1 ml). The solvent was removed completely. The product was analysed by HPLC-MS and purified by preparative HPLC at a purity of <85%.

The following compounds were produced by automated synthesis.

| No. | Starting product S | Starting product A | Name | MS m/z [M + H]+ |
|---|---|---|---|---|
| 1 | S1 | A05 | (4-Benzylpiperidin-1-yl)(6-phenyl-5,6,7,8-tetrahydroimidazo[1,2-a]pyridin-2-yl)methanone | 400.2 |
| 2 | S1 | A08 | N-Benzyl-N-phenethyl-6-phenyl-5,6,7,8-tetrahydroimidazo[1,2-a]pyridine-2-carboxamide | 436.2 |
| 3 | S1 | A17 | (6-Phenyl-5,6,7,8-tetrahydroimidazo[1,2-a]pyridin-2-yl)(1,3,3-trimethyl-6-azabicyclo[3.2.1]octan-6-yl)methanone | 378.2 |
| 4 | S5 | A17 | (6-(3-Fluorophenyl)-5,6,7,8-tetrahydroimidazo[1,2-a]pyridin-2-yl)(1,3,3-trimethyl-6-azabicyclo[3.2.1]octan-6-yl)methanone | 396.2 |
| 5 | S2 | A02 | N-Benzyl-6-(4-methoxy-3,5-dimethylphenyl)-5,6,7,8-tetrahydroimidazo[1,2-a]pyridine-2-carboxamide | 390.2 |
| 6 | S2 | A13 | (4-(2-Fluorophenyl)piperazin-1-yl)(6-(4-methoxy-3,5-dimethylphenyl)-5,6,7,8-tetrahydroimidazo[1,2-a]pyridin-2-yl)methanone | 463.2 |
| 7 | S7 | A19 | (6-(5-Fluoro-2-methoxyphenyl)-5,6,7,8-tetrahydroimidazo[1,2-a]pyridin-2-yl)(4-(3-(trifluoromethyl)phenyl)piperazin-1-yl)methanone | 503.2 |
| 8 | S7 | A05 | (4-Benzylpiperidin-1-yl)(6-(5-fluoro-2-methoxyphenyl)-5,6,7,8-tetrahydroimidazo[1,2-a]pyridin-2-yl)methanone | 448.2 |
| 9 | S7 | A17 | (6-(5-Fluoro-2-methoxyphenyl)-5,6,7,8-tetrahydroimidazo[1,2-a]pyridin-2-yl)(1,3,3-trimethyl-6-azabicyclo[3.2.1]octan-6-yl)methanone | 426.2 |
| 10 | S2 | A01 | (6-(4-Methoxy-3,5-dimethylphenyl)-5,6,7,8-tetrahydroimidazo[1,2-a]pyridin-2-yl)(4-(2-methoxyphenyl)piperazin-1-yl)methanone | 475.3 |
| 11 | S9 | A05 | (4-Benzylpiperidin-1-yl)(6-(4-ethylphenyl)-5,6,7,8-tetrahydroimidazo[1,2-a]pyridin-2-yl)methanone | 428.3 |
| 12 | S8 | A17 | (6-(2,5-Dimethoxyphenyl)-5,6,7,8-tetrahydroimidazo[1,2-a]pyridin-2-yl)(1,3,3-trimethyl-6-azabicyclo[3.2.1]octan-6-yl)methanone | 438.3 |
| 13 | S3 | A13 | (6-(4-Fluoro-3-methylphenyl)-5,6,7,8-tetrahydroimidazo[1,2-a]pyridin-2-yl)(4-(2-fluorophenyl)piperazin-1-yl)methanone | 437.2 |
| 14 | S3 | A26 | 6-(4-Fluoro-3-methylphenyl)-N-(1-phenylethyl)-5,6,7,8-tetrahydroimidazo-[1,2-a]pyridine-2-carboxamide | 378.2 |
| 15 | S2 | A18 | 6-(4-Methoxy-3,5-dimethylphenyl)-N-pentyl-5,6,7,8-tetrahydroimidazo[1,2-a]pyridine-2-carboxamide | 370.2 |
| 16 | S2 | A20 | N-Hexyl-6-(4-methoxy-3,5-dimethylphenyl)-5,6,7,8-tetrahydroimidazo[1,2-a]pyridine-2-carboxamide | 384.3 |
| 17 | S2 | A23 | 6-(4-Methoxy-3,5-dimethylphenyl)-N-(3-(trifluoromethyl)benzyl)-5,6,7,8-tetrahydroimidazo[1,2-a]pyridine-2-carboxamide | 458.2 |
| 18 | S11 | A24 | N-sec-Butyl-6-(4-phenoxyphenyl)-5,6,7,8-tetrahydroimidazo[1,2-a]pyridine-2-carboxamide | 390.2 |
| 19 | S11 | A15 | N-Butyl-6-(4-phenoxyphenyl)-5,6,7,8-tetrahydroimidazo[1,2-a]pyridine-2-carboxamide | 390.2 |
| 20 | S11 | A07 | Ethyl 1-(6-(4-phenoxyphenyl)-5,6,7,8-tetrahydroimidazo[1,2-a]pyridine-2-carbonyl)piperidine-4-carboxylate | 474.2 |

-continued

| No. | Starting product S | Starting product A | Name | MS m/z [M + H]+ |
|---|---|---|---|---|
| 21 | S11 | A21 | (4-Methylpiperidin-1-yl)(6-(4-phenoxyphenyl)-5,6,7,8-tetrahydroimidazo[1,2-a]pyridin-2-yl)methanone | 416.2 |
| 22 | S11 | A10 | Ethyl 1-(6-(4-phenoxyphenyl)-5,6,7,8-tetrahydroimidazo[1,2-a]pyridine-2-carbonyl)piperidine-3-carboxylate | 474.2 |
| 23 | S11 | A11 | 1-(4-(6-(4-Phenoxyphenyl)-5,6,7,8-tetrahydroimidazo[1,2-a]pyridine-2-carbonyl)piperazin-1-yl)ethanone | 445.2 |
| 24 | S11 | A04 | 6-(4-Phenoxyphenyl)-N-(pyridin-3-ylmethyl)-5,6,7,8-tetrahydroimidazo-[1,2-a]pyridine-2-carboxamide | 425.2 |
| 25 | S11 | A12 | (6-(4-Phenoxyphenyl)-5,6,7,8-tetrahydroimidazo[1,2-a]pyridin-2-yl)(pyrrolidin-1-yl)methanone | 388.2 |
| 26 | S11 | A06 | N-Cyclopropyl-6-(4-phenoxyphenyl)-5,6,7,8-tetrahydroimidazo[1,2-a]pyridine-2-carboxamide | 374.2 |
| 27 | S11 | A09 | N-(3,4-Dimethoxyphenethyl)-6-(4-phenoxyphenyl)-5,6,7,8-tetrahydroimidazo[1,2-a]pyridine-2-carboxamide | 498.2 |
| 28 | S11 | A18 | N-Pentyl-6-(4-phenoxyphenyl)-5,6,7,8-tetrahydroimidazo[1,2-a]pyridine-2-carboxamide | 404.2 |
| 29 | S12 | A12 | Pyrrolidin-1-yl(6-m-tolyl-5,6,7,8-tetrahydroimidazo[1,2-a]pyridin-2-yl)methanone | 310.2 |
| 30 | S14 | A12 | (6-(3,5-Bis(trifluoromethyl)phenyl)-5,6,7,8-tetrahydroimidazo[1,2-a]pyridin-2-yl)(pyrrolidin-1-yl)methanone | 432.1 |
| 31 | S15 | A12 | Pyrrolidin-1-yl(6-(3-(trifluoromethyl)phenyl)-5,6,7,8-tetrahydroimidazo[1,2-a]pyridin-2-yl)methanone | 364.2 |
| 32 | S15 | A13 | (4-(2-Fluorophenyl)piperazin-1-yl)(6-(3-(trifluoromethyl)phenyl)-5,6,7,8-tetrahydroimidazo[1,2-a]pyridin-2-yl)methanone | 473.2 |
| 33 | S16 | A12 | (6-(2,4-Dimethoxyphenyl)-5,6,7,8-tetrahydroimidazo[1,2-a]pyridin-2-yl)(pyrrolidin-1-yl)methanone | 356.2 |
| 34 | S17 | A12 | Pyrrolidin-1-yl(6-o-tolyl-5,6,7,8-tetrahydroimidazo[1,2-a]pyridin-2-yl)methanone | 310.2 |
| 35 | S17 | A19 | (6-o-Tolyl-5,6,7,8-tetrahydroimidazo-[1,2-a]pyridin-2-yl)(4-(3-(trifluoromethyl)phenyl)piperazin-1-yl)methanone | 469.2 |
| 36 | S13 | A12 | (6-(2,5-Difluorophenyl)-5,6,7,8-tetrahydroimidazo[1,2-a]pyridin-2-yl)(pyrrolidin-1-yl)methanone | 332.1 |
| 37 | S9 | A12 | (6-(4-Ethylphenyl)-5,6,7,8-tetrahydroimidazo[1,2-a]pyridin-2-yl)(pyrrolidin-1-yl)methanone | 324.2 |
| 38 | S10 | A17 | (6-(4-Fluorophenyl)-5,6,7,8-tetrahydroimidazo[1,2-a]pyridin-2-yl)(1,3,3-trimethyl-6-azabicyclo[3.2.1]octan-6-yl)methanone | 396.2 |
| 39 | S6 | A23 | 6-(4-Methoxyphenyl)-N-(3-(trifluoromethyl)benzyl)-5,6,7,8-tetrahydroimidazo[1,2-a]pyridine-2-carboxamide | 430.2 |
| 40 | S9 | A03 | 6-(4-Ethylphenyl)-N-phenethyl-5,6,7,8-tetrahydroimidazo[1,2-a]pyridine-2-carboxamide | 374.2 |
| 41 | S10 | A05 | (4-Benzylpiperidin-1-yl)(6-(4-fluorophenyl)-5,6,7,8-tetrahydroimidazo[1,2-a]pyridin-2-yl)methanone | 418.2 |
| 42 | S14 | A14 | N-(Benzo[d][1,3]dioxol-5-ylmethyl)-6-(3,5-bis(trifluoromethyl)phenyl)-5,6,7,8-tetrahydroimidazo[1,2-a]pyridine-2-carboxamide | 512.1 |

-continued

| No. | Starting product S | Starting product A | Name | MS m/z [M + H]+ |
|---|---|---|---|---|
| 43 | S14 | A02 | N-Benzyl-6-(3,5-bis(trifluoromethyl)phenyl)-5,6,7,8-tetrahydroimidazo[1,2-a]pyridine-2-carboxamide | 468.1 |
| 44 | S2 | A25 | (6-(4-Methoxy-3,5-dimethylphenyl)-5,6,7,8-tetrahydroimidazo[1,2-a]pyridin-2-yl)(4-(4-methoxyphenyl)-piperazin-1-yl)methanone | 475.3 |
| 45 | S12 | A27 | (4-(2-Ethoxyphenyl)piperazin-1-yl)(6-m-tolyl-5,6,7,8-tetrahydroimidazo[1,2-a]pyridin-2-yl)methanone | 445.3 |
| 46 | S16 | A19 | (6-(2,4-Dimethoxyphenyl)-5,6,7,8-tetrahydroimidazo[1,2-a]pyridin-2-yl)(4-(3-(trifluoromethyl)phenyl)piperazin-1-yl)methanone | 515.2 |
| 47 | S10 | A19 | (6-(4-Fluorophenyl)-5,6,7,8-tetrahydroimidazo[1,2-a]pyridin-2-yl)(4-(3-(trifluoromethyl)phenyl)piperazin-1-yl)methanone | 473.2 |
| 48 | S5 | A19 | (6-(3-Fluorophenyl)-5,6,7,8-tetrahydroimidazo[1,2-a]pyridin-2-yl)(4-(3-(trifluoromethyl)phenyl)piperazin-1-yl)methanone | 473.2 |
| 49 | S2 | A16 | N-(4-Fluorobenzyl)-6-(4-methoxy-3,5-dimethylphenyl)-5,6,7,8-tetrahydro-imidazo[1,2-a]pyridine-2-carboxamide | 408.2 |
| 50 | S4 | A05 | (4-Benzylpiperidin-1-yl)(6-(3-methoxyphenyl)-5,6,7,8-tetrahydro-imidazo[1,2-a]pyridin-2-yl)methanone | 430.2 |
| 51 | S5 | A22 | 6-(3-Fluorophenyl)-N-(4-phenylbutan-2-yl)-5,6,7,8-tetrahydroimidazo[1,2-a]pyridine-2-carboxamide | 392.2 |
| 52 | S9 | A22 | 6-(4-Ethylphenyl)-N-(4-phenylbutan-2-yl)-5,6,7,8-tetrahydroimidazo[1,2-a]pyridine-2-carboxamide | 402.2 |

Equipment:

Waters 1525 HPLC system: high-pressure binary HPLC pump with integrated splitter, MUX-UV 2488 detector (Waters Corp.) and in-house-developed autosampler based on a Cavro RSP 9452 (Cavro Scientific Inst., Inc.) robot workstation.

ZQ2000 MS instrument (Waters Corp.) with ESI interface integrated with MUX (Waters Corp.)

| Method: | |
|---|---|
| HPLC column: | |
| LiChroCART 30-4 Purospher STAR RP-18, end-capped, 3 μm (Merck) | |
| Gradient: | |
| Eluent (A): | Acetonitrile-H$_2$O = 5:95 with 20 mM HCOONH$_4$/NH$_4$OH buffer, pH 7.4 |
| Eluent (B): | Acetonitrile-H$_2$O = 80:20 with 20 mM HCOONH$_4$/NH$_4$OH buffer, pH 7.4 |
| Gradient program: | |

| | Min. | A % | B % |
|---|---|---|---|
| Column temperature: | 0.0 | 95 | 5 |
| Flow rate: | 2.5 | 5 | 95 |
| Sample concentration: | 4.3 | 5 | 95 |
| | 4.4 | 95 | 5 |
| Solvent samples: | 5.0 | 95 | 5 |
| Injection volume: | 2.5 μl | | |
| Detection: | UV 220 nm | | |

Solid Substances (6-Phenyl-5,6,7,8-tetrahydroimidazo[1,2-a]pyridin-2-yl)(4-(3-(trifluoromethyl)phenyl)piperazin-1-yl) methanone 53

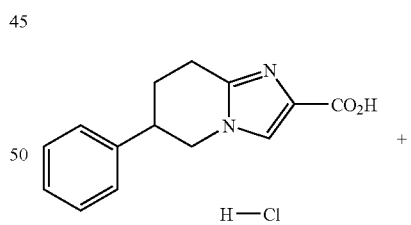

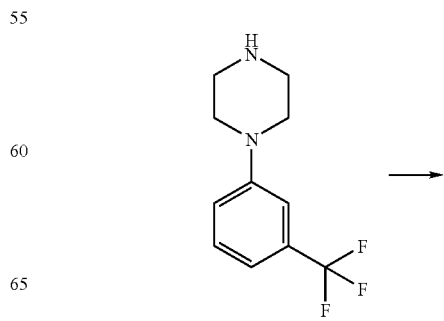

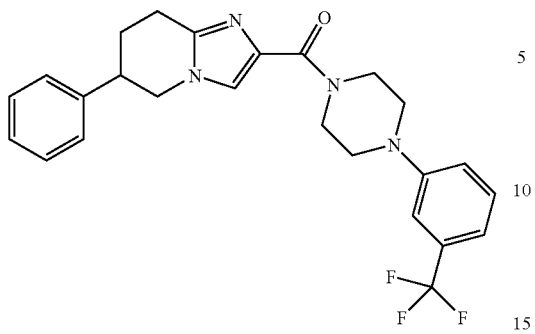
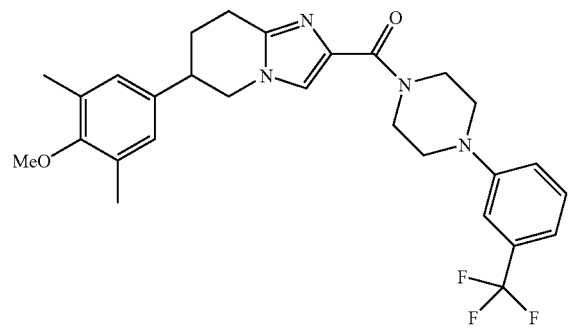

TBTU (276 mg; 0.86 mmol) and N-methylmorpholine (237 µl; 218 mg; 2.15 mmol) were added to a solution of 6-phenyl-5,6,7,8-tetrahydroimidazo[1,2-a]pyridine-2-carboxylic acid hydrochloride (200 mg; 0.72 mmol) in DMF (1 ml). The reaction mixture was stirred vigorously for 30 min at room temperature and then 1-(3-trifluoromethylphenyl)piperazine (162 µl; 198 mg; 0.86 mmol) was added. The reaction mixture was stirred for 4 h at room temperature, then poured onto water and extracted with chloroform. The organic phase was dried over MgSO$_4$, filtered and concentrated to small volume. The raw product was purified by column chromatography on silica gel (chloroform). Yield: 191 mg (59%).

$^1$H NMR (600 MHz, DMSO-d$_6$) d ppm 2.02-2.14 (m, 2H) 2.21 (s, 6H) 2.46-2.55 (m, 3H) 2.79-2.97 (m, 2H) 3.06-3.19 (m, 1H) 3.23-3.35 (m, 5H) 3.64 (s, 3H) 3.92 (t, J=11.71 Hz, 1H) 4.22 (dd, J=12.46, 4.91 Hz, 1H) 7.01 (s, 2H) 7.09 (d, J=6.80 Hz, 1H) 7.21 (br. s., 1H) 7.25 (d, J=8.31 Hz, 1H) 7.43 (t, J=7.93 Hz, 1H) 7.56 (br. s., 1H); MS: m/z 455.2 [M+H]$^+$ TBTU (240 mg; 0.75 mmol) and N-methylmorpholine (206 µl; 189 mg; 1.87 mmol) were added to a solution of 6-(4-methoxy-3,5-dimethylphenyl)-5,6,7,8-tetrahydroimidazo[1,2-a]pyridine-2-carboxylic acid hydrochloride (210 mg; 0.63 mmol) in DMF (1 ml). The reaction mixture was stirred vigorously for 30 min at room temperature and then 1-(3-trifluoromethylphenyl)piperazine (140 µl; 172 mg; 0.75 mmol) was added. The reaction mixture was stirred for 4 h at room temperature, then poured onto water and extracted with chloroform. The organic phase was dried over MgSO$_4$, filtered and concentrated to small volume. The raw product was purified by column chromatography on silica gel (chloroform). Yield: 198 mg (62%).

$^1$H NMR (600 MHz, DMSO-d$_6$) d ppm 2.00-2.14 (m, 2H) 2.21 (s, 6H) 2.78-2.97 (m, 2H) 3.08-3.20 (m, 1H) 3.24-3.30 (m, 8H) 3.64 (s, 3H) 3.92 (t, J=11.71 Hz, 1H) 4.22 (dd, J=12.46, 4.91 Hz, 1H) 7.01 (s, 2H) 7.09 (d, J=6.80 Hz, 1H) 7.21 (br. s., 1H) 7.25 (d, J=8.31 Hz, 1H) 7.43 (t, J=7.93 Hz, 1H) 7.56 (s, 1H); MS: m/z 513.2 [M+H]$^+$ (6-(4-Methoxy-3,5-dimethylphenyl)-5,6,7,8-tetrahydroimidazo[1,2-a]pyridin-2-yl)(4-(3-(trifluoromethyl)phenyl)piperazin-1-yl)methanone 54

(4-Benzylpiperidin-1-yl)(6-(4-methoxy-3,5-dimethylphenyl)-5,6,7,8-tetrahydroimidazo-[1,2-a]pyridin-2-yl)methanone 55

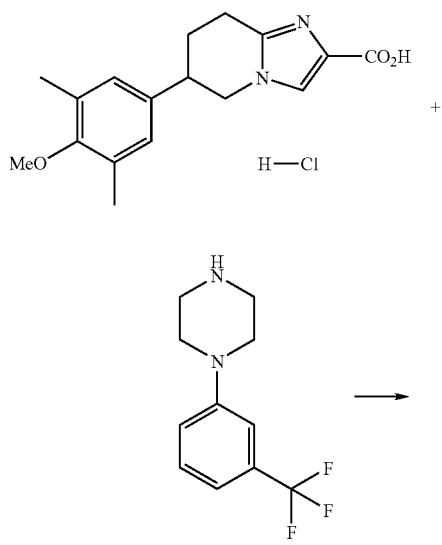

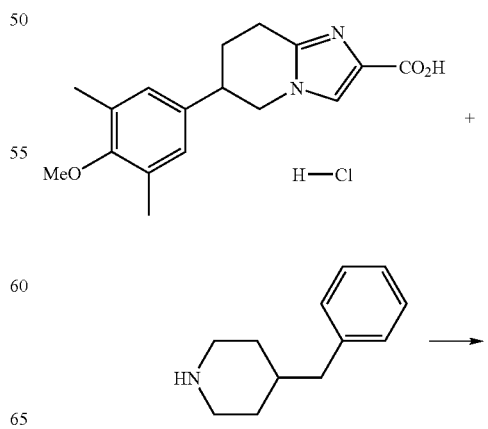

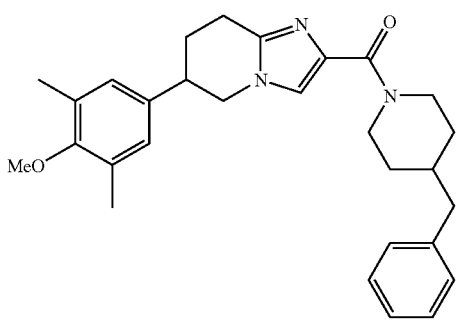

TBTU (212 mg; 0.66 mmol) and N-methylmorpholine (181 µl; 167 mg; 1.65 mmol) were added to a solution of 6-(4-methoxy-3,5-dimethylphenyl)-5,6,7,8-tetrahydroimidazo[1,2-a]pyridine-2-carboxylic acid hydrochloride (165 mg; 0.49 mmol) in DMF (1 ml). The reaction mixture was stirred vigorously for 30 min at room temperature and then 4-benzylpiperidine (116 µl; 116 mg; 0.7 mmol) was added. The reaction mixture was stirred for 4 h at room temperature and then poured onto water. The precipitated solid was filtered out. Yield: 182 mg (81%)

$^1$H NMR (600 MHz, DMSO-d$_6$) d ppm 0.97-1.28 (m, 2H) 1.51-1.69 (m, 2H) 1.72-1.87 (m, 1H) 1.97-2.11 (m, 2H) 2.21 (s, 6H) 2.50-2.56 (m, 4H) 2.71-2.99 (m, 4H) 3.01-3.21 (m, 1H) 3.63 (s, 3H) 3.77-3.99 (m, 1H) 4.10-4.26 (m, 1H) 7.00 (s, 2H) 7.09-7.22 (m, 3H) 7.28 (t, J=7.18 Hz, 2H) 7.45 (br. s., 1H); MS: m/z 458.3 [M+H]$^+$ (6-(4-Methoxy-3,5-dimethylphenyl)-5,6,7,8-tetrahydroimidazo[1,2-a]pyridin-2-yl)(1,3,3-trimethyl-6-azabicyclo[3.2.1]octan-6-yl)methanone 56

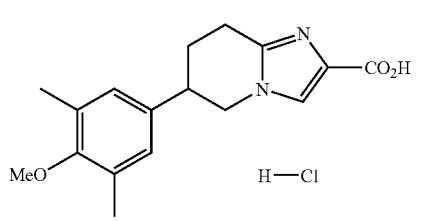

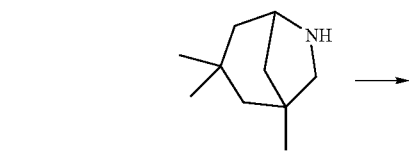

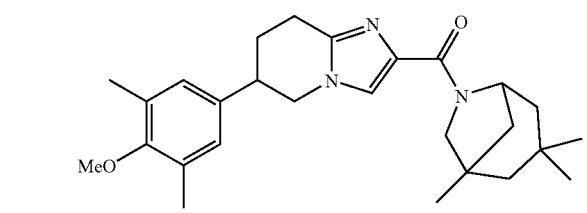

TBTU (212 mg; 0.66 mmol) and N-methylmorpholine (181 µl; 167 mg; 1.65 mmol) were added to a solution of 6-(4-methoxy-3,5-dimethylphenyl)-5,6,7,8-tetrahydroimidazo[1,2-a]pyridine-2-carboxylic acid hydrochloride (165 mg; 0.49 mmol) in DMF (1 ml). The reaction mixture was stirred vigorously for 30 min at room temperature and then 1,3,3-trimethyl-6-azabicyclo[3.2.1]octane (112 µl; 101 mg; 0.7 mmol) was added. The reaction mixture was stirred for 4 h at room temperature and then poured onto water. The precipitated solid was filtered.

Yield: 180 mg (84%) mixture of diastereomers. ESI-MS: m/z 436.3 [M+H]$^+$.

(4-Benzylpiperidin-1-yl)(6-(4-fluoro-3-methylphenyl)-5,6,7,8-tetrahydroimidazo[1,2-a]pyridin-2-yl)methanone 57

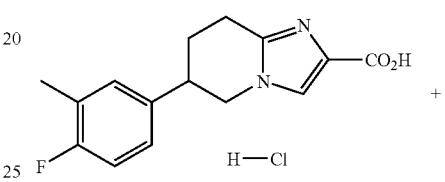

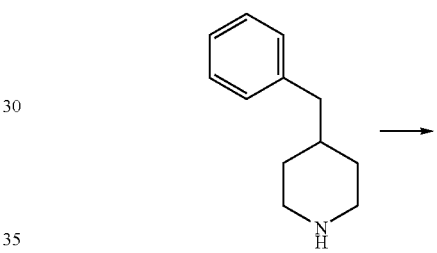

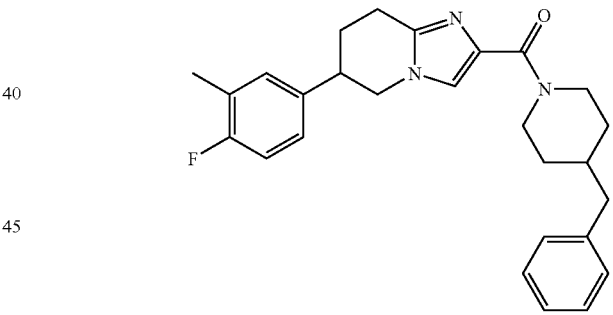

TBTU (295 mg; 0.92 mmol) and N-methylmorpholine (253 µl; 232 mg; 2.3 mmol) were added to a solution of 6-(4-fluoro-3-methylphenyl)-5,6,7,8-tetrahydro-imidazo[1,2-a]pyridine-2-carboxylic acid hydrochloride (210 mg; 0.68 mmol) in DMF (1 ml). The reaction mixture was stirred vigorously for 30 min at room temperature and then 4-benzylpiperidine (162 µl; 161 mg; 0.9 mmol) was added. The reaction mixture was stirred for 4 h at room temperature and then poured onto water. The precipitated solid was filtered out and washed with petroleum ether. Yield: 205 mg (72%)

$^1$H NMR (600 MHz, DMSO-d$_6$) d ppm 1.02-1.18 (m, 2H) 1.54-1.66 (m, 2H) 1.73-1.85 (m, 1H) 2.02-2.14 (m, 2H) 2.23 (s, 3H) 2.51-2.56 (m, 2H) 2.76-2.97 (m, 4H) 3.16-3.26 (m, 1H) 3.25-3.30 (m, 2H) 3.92 (t, J=11.71 Hz, 1H) 4.21 (dd, J=12.46, 4.91 Hz, 1H) 7.10 (t, J=9.06 Hz, 1H) 7.14-7.23 (m, 4H) 7.28 (t, J=6.80 Hz, 3H) 7.46 (s, 1H)); MS: m/z 432.2 [M+H]$^+$

(6-(4-Fluoro-3-methylphenyl)-5,6,7,8-tetrahydroimidazo[1,2-a]pyridin-2-yl)(4-(3-(trifluoromethyl)phenyl)piperazin-1-yl)methanone 58

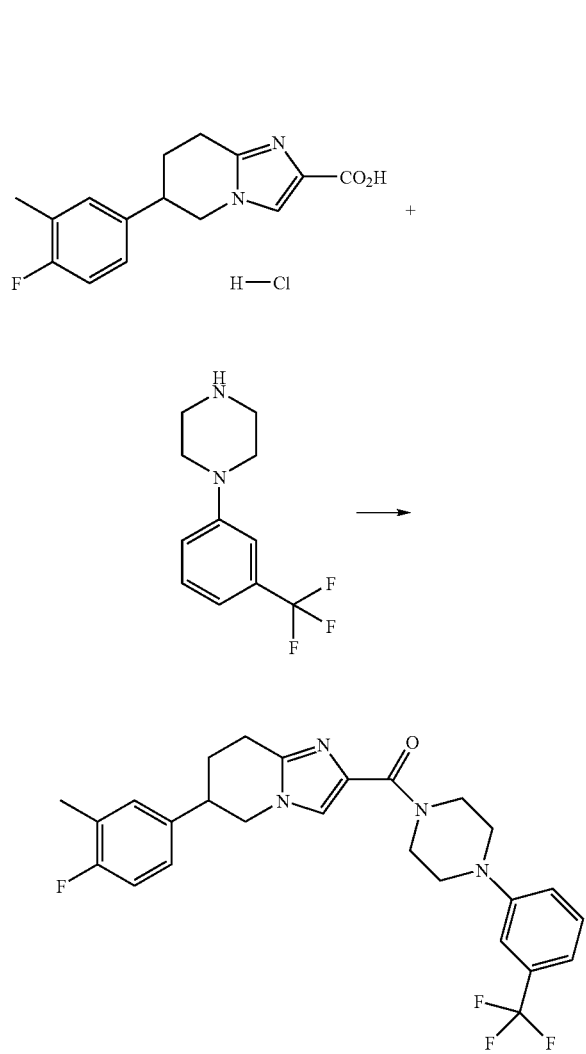

TBTU (295 mg; 0.92 mmol) and N-methylmorpholine (253 µl; 232 mg; 2.3 mmol) were added to a solution of 6-(4-fluoro-3-methylphenyl)-5,6,7,8-tetrahydroimidazo[1,2-a]pyridine-2-carboxylic acid hydrochloride (210 mg; 0.68 mmol) in DMF (1 ml). The reaction mixture was stirred vigorously for 30 min at room temperature and then 1-(3-trifluoromethylphenyl)piperazine (173 µl; 212 mg; 0.92 mmol) was added. The reaction mixture was stirred for 4 h at room temperature and poured onto water. The precipitated solid was purified by column chromatography on silica gel (chloroform). Yield: 166 mg (50%)

$^1$H NMR (600 MHz, DMSO-d$_6$) d ppm 2.00-2.19 (m, 2H) 2.23 (s, 3H) 2.78-3.02 (m, 2H) 3.11-3.29 (m, 5H) 3.55-3.89 (m, 2H) 3.95 (t, J=11.71 Hz, 1H) 4.25 (dd, J=12.46, 4.91 Hz, 1H) 4.30-4.66 (m, 2H) 7.01-7.16 (m, 2H) 7.17-7.24 (m, 2H) 7.25 (d, J=9.06 Hz, 1H) 7.29 (d, J=7.55 Hz, 1H) 7.43 (t, J=7.93 Hz, 1H) 7.57 (s, 1H); MS: m/z 487.2 [M+H]$^+$

(4-Benzhydrylpiperazin-1-yl)(6-(4-methoxy-3,5-dimethylphenyl)-5,6,7,8-tetrahydroimidazo[1,2-a]pyridin-2-yl)methanone 59

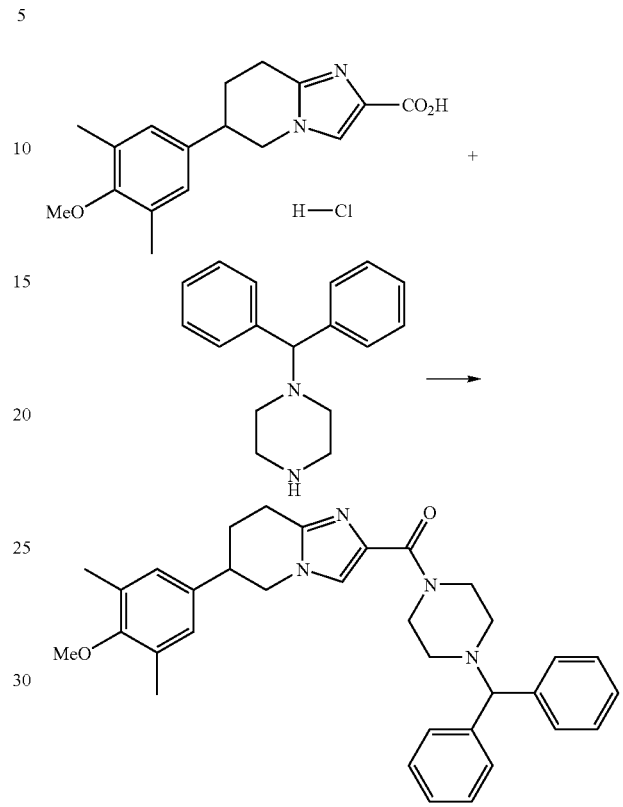

TBTU (212 mg; 0.66 mmol) and N-methylmorpholine (181 µl; 167 mg; 1.65 mmol) were added to a solution of 6-(4-methoxy-3,5-dimethylphenyl)-5,6,7,8-tetrahydroimidazo[1,2-a]pyridine-2-carboxylic acid hydrochloride (165 mg; 0.49 mmol) in DMF (1 ml). The reaction mixture was stirred vigorously for 30 min at room temperature and then diphenylmethylpiperazine (166 mg; 0.7 mmol) was added. The reaction mixture was stirred for 4 h at room temperature and poured onto water. The precipitated solid was filtered. Yield: 232 mg (88%).

$^1$H NMR (600 MHz, DMSO-d$_6$) d ppm 1.96-2.12 (m, 2H) 2.20 (s, 6H) 2.26-2.38 (m, 4H) 2.45-2.54 (m, 2H) 2.72-2.94 (m, 2H) 3.01-3.18 (m, 1H) 3.55-3.72 (m, 4H) 3.87 (t, J=111.71 Hz, 1H) 4.18 (dd, J=12.09, 4.53 Hz, 2H) 4.35 (s, 1H) 6.99 (s, 2H) 7.20 (t, J=7.18 Hz, 2H) 7.30 (t, J=7.55 Hz, 4H) 7.43 (d, J=7.55 Hz, 4H) 7.47 (s, 1H); MS: m/z 535.3 [M+H]$^+$

6-(3-Methoxyphenyl)-N-(4-phenylbutan-2-yl)-5,6,7,8-tetrahydroimidazo[1,2-a]pyridine-2-carboxamide 60

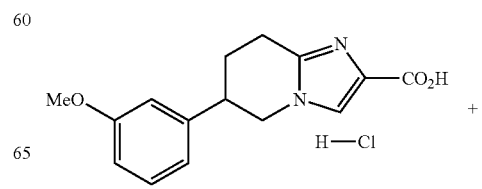

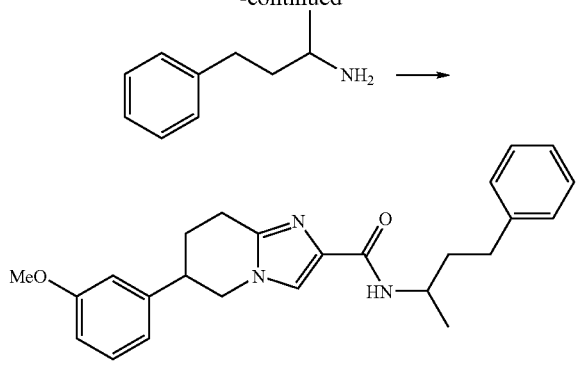

TBTU (310 mg; 0.97 mmol) and N-methylmorpholine (267 µl; 245 mg; 2.4 mmol) were added to a solution of 6-(3-methoxyphenyl)-5,6,7,8-tetrahydroimidazo[1,2-a]pyridine-2-carboxylic acid hydrochloride (250 mg; 0.8 mmol) in DMF (1 ml). The reaction mixture was stirred vigorously for 30 min at room temperature and then 1-methyl-3-phenylpropylamine (157 µl; 145 mg; 1.0 mmol) was added. The reaction mixture was stirred for 4 h at room temperature, poured onto water and extracted with chloroform. The organic phase was dried over MgSO$_4$, filtered and concentrated to small volume. The raw product was purified by column chromatography on silica gel (chloroform). Yield: 183 mg (56%)

$^1$H NMR (600 MHz, DMSO-d$_6$) d ppm 1.14 (d, J=6.04 Hz, 3H) 1.63-1.77 (m, 1H) 1.81-1.91 (m, 1H) 2.06-2.19 (m, 2H) 2.52-2.63 (m, 2H) 2.80-2.96 (m, 2H) 3.18-3.27 (m, 1H) 3.75 (s, 3H) 3.93-4.05 (m, 2H) 4.25 (dd, J=12.09, 4.53 Hz, 1H) 6.84 (d, J=8.31 Hz, 1H) 6.90-6.98 (m, 2H) 7.12-7.22 (m, 3H) 7.23-7.31 (m, 3H) 7.50 (s, 1H) 7.58 (d, J=8.31 Hz, 1H); MS: m/z 404.2 [M+H]+

Synthesis of Compounds 61 to 88

TBTU (1.5 eq) and N-methylmorpholine (3.5 eq) were added to a solution of carboxylic acid (500 mg) in DMF (2.5 ml). The reaction mixture was stirred vigorously for 30 min at room temperature and then the corresponding amine (1.1 eq) was added. The reaction mixture was stirred overnight at room temperature. On completion of the reaction the mixture was diluted with ethyl acetate and washed successively with saturated ammonium chloride solution, saturated sodium chloride solution, sodium hydrogen carbonate solution and saturated sodium chloride solution. The organic phase was dried over sodium sulfate and concentrated to small volume. The crude product was purified on silica gel by column chromatography using the mobile solvents specified in the following table.

| No. | Structure | Yield % | Mobile solvent | MS m/z [M + H]+ |
|---|---|---|---|---|
| 61 | (4-Benzylpiperidin-1-yl)(6-(3-fluorophenyl)-5,6,7,8-tetrahydroimidazo[1,2-a]pyridin-2-yl)methanone | 80 | 80% ethyl acetate in hexane | 418.2 |
| 62 | (6-(4-Fluoro-3-methylphenyl)-5,6,7,8-tetrahydroimidazo[1,2-a]pyridin-2-yl)(4-(4-(trifluoromethyl)phenyl)piperazin-1-yl)methanone | 28 | 60% ethyl acetate in hexane | 487.2 |
| 63 | (6-(4-Fluoro-3-methylphenyl)-5,6,7,8-tetrahydroimidazo[1,2-a]pyridin-2-yl)(4-(4-fluorophenyl)piperazin-1-yl)methanone | 32 | 5% methanol in DCM | 437.2 |

| No. | Structure | Yield % | Mobile solvent | MS m/z [M + H]+ |
|---|---|---|---|---|
| 64 | (6-(4-Fluoro-3-methylphenyl)-5,6,7,8-tetrahydroimidazo[1,2-a]pyridin-2-yl)(4-(4-methylphenyl)piperazin-1-yl)methanone | 68 | 70% ethyl acetate in hexane | 433.2 |
| 65 | (6-(4-Fluoro-3-methylphenyl)-5,6,7,8-tetrahydroimidazo[1,2-a]pyridin-2-yl)(4-(3-methylphenyl)piperazin-1-yl)methanone | 70 | 70% ethyl acetate in hexane | 433.2 |
| 66 | (4-Butylpiperazin-1-yl)(6-(4-fluoro-3-methylphenyl)-5,6,7,8-tetrahydroimidazo[1,2-a]pyridin-2-yl)methanone | 56 | 80% ethyl acetate in hexane | 399.2 |
| 67 | (4-Benzhydrylpiperidin-1-yl)(6-(4-fluoro-3-methylphenyl)-5,6,7,8-tetrahydroimidazo[1,2-a]pyridin-2-yl)methanone | 67 | 80% ethyl acetate in hexane | 508.3 |
| 68 | N-(Cyclohexylmethyl)-6-(4-fluoro-3-methylphenyl)-5,6,7,8-tetrahydroimidazo[1,2-a]pyridine-2-carboxamide | 54 | 70% ethyl acetate in hexane | 370.2 |

| No. | Structure | Yield % | Mobile solvent | MS m/z [M + H]+ |
|---|---|---|---|---|
| 69 | (6-(4-Methoxyphenyl)-5,6,7,8-tetrahydroimidazo[1,2-a]pyridin-2-yl)(4-(3-(trifluoromethyl)phenyl)piperazin-1-yl)methanone | 40 | 70% ethyl acetate in hexane | 485.2 |
| 70 | (4-Benzylpiperidin-1-yl)(6-m-tolyl-5,6,7,8-tetrahydroimidazo[1,2-a]pyridin-2-yl)methanone | 58 | 80% ethyl acetate in hexane | 414.2 |
| 71 | (6-(3-Methoxyphenyl)-5,6,7,8-tetrahydroimidazo[1,2-a]pyridin-2-yl)(4-(3-(trifluoromethyl)phenyl)piperazin-1-yl)methanone | 76 | 90% ethyl acetate in hexane | 485.2 |
| 72 | 6-(4-Fluoro-3-methylphenyl)-N-(4-phenylbutan-2-yl)-5,6,7,8-tetrahydroimidazo[1,2-a]pyridine-2-carboxamide | 66 | 80% ethyl acetate in hexane | 406.2 |
| 73 | 4-Benzylpiperidin-1-yl)(6-p-tolyl-5,6,7,8-tetrahydroimidazo[1,2-a]pyridin-2-yl)methanone | 22 | 80% ethyl acetate in hexane | 414.2 |

-continued

| No. | Structure | Yield % | Mobile solvent | MS m/z [M + H]+ |
|---|---|---|---|---|
| 74 | (6-p-Tolyl-5,6,7,8-tetrahydroimidazo[1,2-a]pyridin-2-yl)(4-(3-(trifluoromethyl)phenyl)piperazin-1-yl)methanone | 19 | 80% ethyl acetate in hexane | 469.2 |
| 75 | (6-m-Tolyl-5,6,7,8-tetrahydroimidazo[1,2-a]pyridin-2-yl)(4-(3-(trifluoromethyl)phenyl)piperazin-1-yl)methanone | 33 | 80% ethyl acetate in hexane | 469.2 |
| 76 | (4-Benzylpiperidin-1-yl)(6-(4-methoxyphenyl)-5,6,7,8-tetrahydroimidazo[1,2-a]pyridin-2-yl)methanone | 35 | 75% ethyl acetate in hexane | 430.2 |
| 77 | (6-(3,5-Dimethylphenyl)-5,6,7,8-tetrahydroimidazo[1,2-a]pyridin-2-yl)(4-(3-(trifluoromethyl)phenyl)piperazin-1-yl)methanone | 50 | 80% ethyl acetate in hexane | 483.2 |
| 78 | N-(1-(3,5-Dimethylphenyl)ethyl)-6-(4-fluoro-3-methylphenyl)-5,6,7,8-tetrahydroimidazo[1,2-a]pyridine-2-carboxamide | 41 | 75% ethyl acetate in hexane | 406.2 |

| No. | Structure | Yield % | Mobile solvent | MS m/z [M + H]+ |
|---|---|---|---|---|
| 79 | (6-(3,4-Difluorophenyl)-5,6,7,8-tetrahydroimidazo[1,2-a]pyridin-2-yl)(4-(3-(trifluoromethyl)phenyl)piperazin-1-yl)methanone | | | 491.2 |
| 80 | (4-Benzylpiperazin-1-yl)(6-(4-fluoro-3-methylphenyl)-5,6,7,8-tetrahydroimidazo[1,2-a]pyridin-2-yl)methanone | | | 433.2 |
| 81 | (6-(4-Phenoxyphenyl)-5,6,7,8-tetrahydroimidazo[1,2-a]pyridin-2-yl)(4-(3-(trifluoromethyl)phenyl)piperazin-1-yl)methanone | | | 547.2 |
| 82 | (6-(4-(Benzyloxy)phenyl)-5,6,7,8-tetrahydroimidazo[1,2-a]pyridin-2-yl)(4-(3-(trifluoromethyl)phenyl)piperazin-1-yl)methanone | | | 561.2 |
| 83 | (6-(4-Fluoro-3-methylphenyl)-5,6,7,8-tetrahydroimidazo[1,2-a]pyridin-2-yl)(4-(3-fluorophenyl)piperazin-1-yl)methanone | 66 | 80% ethyl acetate in hexane | 436.2 |

-continued

| No. | Structure | Yield % | Mobile solvent | MS m/z [M + H]+ |
|---|---|---|---|---|
| 84 | (6-(4-Fluoro-3-methylphenyl)-5,6,7,8-tetrahydroimidazo[1,2-a]pyridin-2-yl)(1,3,3-trimethyl-6-azabicyclo[3.2.1]octan-6-yl)methanone | 86 | 80% ethyl acetate in hexane | 409.3 |
| 85 | (6-(4-Fluoro-3-methylphenyl)-5,6,7,8-tetrahydroimidazo[1,2-a]pyridin-2-yl)(4-(3-(trifluoromethyl)phenyl)piperidin-1-yl)methanone | 62 | 80% ethyl acetate in hexane | 485.2 |
| 86 | 6-(4-Fluoro-3-methylphenyl)-N-(4-(3-(trifluoromethyl)phenyl)butan-2-yl)-5,6,7,8-tetrahydroimidazo[1,2-a]pyridine-2-carboxamide | 29 | 80% ethyl acetate in hexane | 473.2 |
| 87 | 6-(4-Fluoro-3-methylphenyl)-N-methyl-N-(4-(3-(trifluoromethyl)phenyl)butan-2-yl)-5,6,7,8-tetrahydroimidazo[1,2-a]pyridine-2-carboxamide | 48 | 80% ethyl acetate in hexane | 487.2 |
| 88 | N-(2-Cyclohexylethyl)-6-(4-fluoro-3-methylphenyl)-5,6,7,8-tetrahydroimidazo[1,2-a]pyridine-2-carboxamide | | | 383.2 |

N-(2-Cyclohexylethyl)-6-(4-fluoro-3-methylphenyl)-5,6,7,8-tetrahydroimidazo[1,2-a]pyridine-2-carboxamide

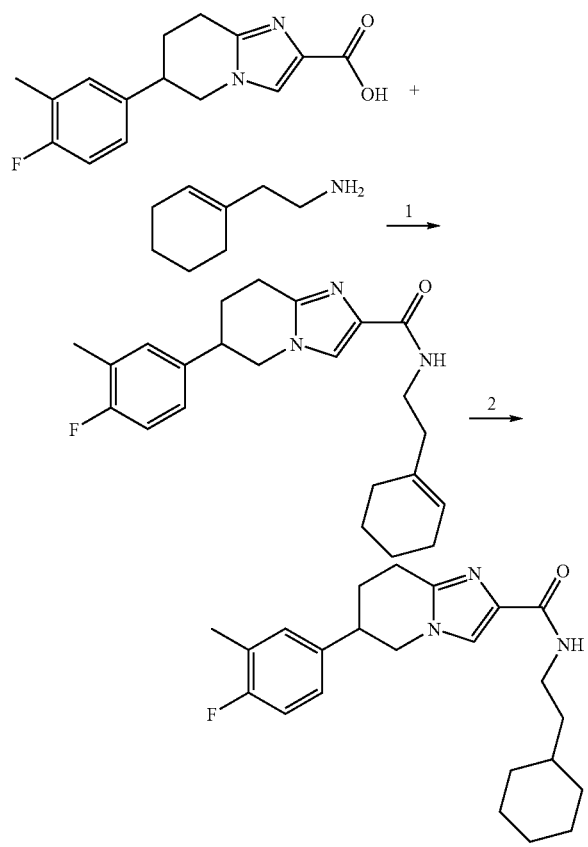

Stage 1. TBTU (1.5 eq) and N-methylmorpholine (3.5 eq) were added to a solution of carboxylic acid (500 mg) in DMF (2.5 ml). The reaction mixture was stirred vigorously for 30 min at room temperature and then the corresponding amine (1.1 eq) was added. The reaction mixture was stirred overnight at room temperature. On completion of the reaction the mixture was diluted with ethyl acetate and washed successively with saturated ammonium chloride solution, saturated sodium chloride solution, sodium hydrogen carbonate solution and saturated sodium chloride solution. The organic phase was dried over sodium sulfate and concentrated to small volume. The crude product was crystallized out of hexane/diethyl ether. Yield: 53%.

Stage 2. The amide was dissolved in ethanol and Pd (10% on carbon, 90 mg/mmol) was added. The reaction batch was stirred for 24 h at room temperature under a hydrogen atmosphere. The reaction mixture was filtered over diatomaceous earth and concentrated to small volume. The product was used in a further process without further purification.

Biological Data

Fluorescence Assay Using a Voltage-Sensitive Dye

Human CHO-K1 cells expressing KCNQ2/3 channels are cultivated adherently at 37° C., 5% $CO_2$ and 95% humidity in cell culture bottles (e.g. 80 cm² TC flasks, Nunc) with MEM Alpha Medium (1×, liquid, Invitrogen, #22571), 10% foetal calf serum (FCS) (Invitrogen, #10270-106, heat-inactivated) and the necessary selection antibiotics. Before being spread out for the measurements, the cells are washed with a 1×DPBS buffer without $Ca^{2+}/Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Schärfe System) in order subsequently to apply 20,000 cells/well/100 μl of the described nutrient medium to 96-well measuring plates of the Corning™ CellBIND™ type (flat clear-bottom black polystyrene microplates, #3340). Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red bulk format part R8123 for FLIPR, Molecular Devices™) is prepared by dissolving the contents of a vessel of Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 μl of ES buffer, then covered with a layer of 100 μl of the dye solution prepared above and incubated for 45 min at room temperature with exclusion of light.

The fluorescence measurements are carried out with a BMG Labtech FLUOstar™ or BMG Labtech POLARstar™ instrument (525 nm excitation, 560 nm emission, bottom-read mode). After incubation of the dye, 50 μl of the substances to be tested in the desired concentrations, or 50 μl of ES buffer for control purposes, are introduced into separate cavities of the measuring plate and incubated for 30 min at room temperature whilst being shielded from light. The fluorescence intensity of the dye is then measured for 5 min and the fluorescence value $F_1$ of each well is thus determined at a given, constant time. 15 μl of a 100 mM KCl solution (final concentration 92 mM) are then added to each well. The change in fluorescence is subsequently measured until all relevant measured values have been obtained (mainly 5-30 min). At a given time after KCl application, a fluorescence value $F_2$ is determined, in this case at the time of the fluorescence peak.

For calculation, the fluorescence intensity $F_2$ is compared with the fluorescence intensity $F_1$, and the agonistic activity of the target compound on the potassium channel is determined therefrom. $F_2$ and $F_1$ are calculated as follows:

$$\left(\frac{F_2 - F_1}{F_1}\right) \times 100 = \frac{\Delta F}{F}(\%)$$

In order to determine whether a substance has an agonistic activity, $$\frac{\Delta F}{F},$$

for example, can be compared with $$\left(\frac{\Delta F}{F}\right)_K$$

of control cells.

$$\left(\frac{\Delta F}{F}\right)_K$$

is determined by adding to the reaction batch only the buffer solution instead of the substance to be tested, determining the value $F_{1K}$ of the fluorescence intensity, adding the potassium ions as described above and measuring a value $F_{2K}$ of the fluorescence intensity. Then $F_{2K}$ and $F_{1K}$ are calculated as follows:

$$\left(\frac{F_{2K} - F_{1K}}{F_{1K}}\right) \times 100 = \left(\frac{\Delta F}{F}\right)_K (\%)$$

A substance has an agonistic activity on the potassium channel when $$\frac{\Delta F}{F}$$

is greater than $$\left(\frac{\Delta F}{F}\right)_K:$$

$$\frac{\Delta F}{F} \rangle \left(\frac{\Delta F}{F}\right)_K$$

Independently of the comparison of $$\frac{\Delta F}{F} \text{ with } \left(\frac{\Delta F}{F}\right)_K,$$

it is also possible to conclude that a target compound has an agonistic activity if an increase in $$\frac{\Delta F}{F}$$

is to be observed as the dosage of the target compound increases. Calculations of $EC_{50}$ and $IC_{50}$ values are carried out with the aid of Prism 4 software (GraphPad Software™).

| No. | % Stimulation [10 µmol] Average | $EC_{50}$ [µM] |
|---|---|---|
| 1 | 16.2 | |
| 2 | 20.0 | |
| 3 | 16.7 | |
| 4 | 20.7 | |
| 5 | 15.5 | |
| 6 | | 7.4 |
| 7 | 30.0 | |
| 8 | 29.1 | |
| 9 | | 11.92 |
| 10 | 15.7 | |
| 11 | 38.5 | |
| 12 | 51.8 | |
| 13 | 18.0 | |
| 14 | 24.7 | |
| 15 | 16.8 | |
| 16 | | 3.95 |
| 17 | 18.5 | |
| 18 | 18.6 | |
| 19 | | 6.21 |
| 20 | | 11.61 |
| 21 | | 8.4 |
| 22 | 18.0 | |
| 23 | | 5.81 |
| 24 | | 6.14 |
| 25 | | 2.33 |
| 26 | 17.4 | |
| 27 | | 6.35 |
| 28 | | 9.38 |
| 29 | 26.2 | |
| 30 | 20.9 | |
| 31 | 17.6 | |
| 32 | 21.2 | |
| 33 | 24.5 | |
| 34 | 32.2 | |
| 35 | 20.9 | |
| 36 | 21.7 | |
| 37 | 15.5 | |
| 38 | 25.9 | |
| 39 | 17.8 | |
| 40 | 16.6 | |
| 41 | 29.4 | |
| 42 | 18.1 | |
| 43 | 16.3 | |
| 44 | 27.5 | |
| 45 | | 7.98 |
| 46 | | 3.98 |
| 47 | 63.5 | |
| 48 | 33.0 | |
| 49 | 15.1 | |
| 50 | 25.7 | |
| 51 | 16.2 | |
| 52 | 34.2 | |
| 53 | | 8.34 |
| 54 | | 2.45 |
| 55 | | 5.42 |
| 56 | | 11.31 |
| 57 | | 9.71 |
| 58 | | 4.46 |
| 59 | | 8.4 |
| 60 | | 6.4 |
| 61 | 82.180 | |
| 62 | 40.840 | |
| 63 | 96.670 | |
| 64 | 46.720 | |
| 65 | 131.557 | |
| 66 | | |
| 67 | 33.307 | |
| 68 | 25.127 | |
| 69 | 30.060 | |
| 70 | 123.123 | |
| 71 | 115.307 | |
| 72 | 103.377 | |
| 73 | 88.763 | |
| 74 | 51.927 | |
| 75 | 126.850 | |
| 76 | 65.087 | |
| 77 | | 0.08 |
| 78 | 29.653 | |
| 79 | 125.493 | |
| 80 | 33.123 | |
| 81 | | |
| 82 | 32.733 | |
| 83 | | 6.5 |
| 84 | 37.873 | |
| 85 | 120.005 | |
| 86 | | 1.2 |
| 87 | 48.435 | |
| 88 | 47.930 | |

List Of Abbreviations
CDI 1,1'-carbonyl diimidazole
d day(s)
dba dibenzylidene acetone
DCE 1,2-dichloroethane DCC N,N'-dicyclohexyl carbodiimide
DCM dichloromethane
DIEA diisopropylethylamine
DMA N,N-dimethylacetamide
DMAP 4-(dimethylamino)pyridine
DMF dimethylformamide
dppf 1,1'-bis(diphenylphosphinoferrocene)
EDCI N-(3-dimethylaminopropyl)-N'-ethyl carbodiimide
EDTA ethylenediamine-N,N,N',N'-tetraacetic acid
h hour(s)
HBTU O-(benzotriazol-1-yl)-N,N,N',N'-tetramethyluronium hexafluorophosphate
HOBt 1-hydroxy-1H-benzotriazole
M molar
min minute(s)
N normal
OAc acetate
P(Cy)$_3$ tricyclohexylphosphine
P(o-tolyl)$_3$ tri-o-tolylphosphine
PPh$_3$ triphenylphosphine
quant. quantitative
TBTU O-(benzotriazol-1-yl)-N,N,N'N'-tetramethyluronium tetrafluoroborate
TEA triethylamine
TFA trifluoroacetic acid
THF tetrahydrofuran The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted tetrahydroimidazopyridine compound corresponding to formula I:

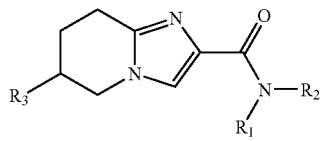

wherein
R$^1$ and R$^2$ each independently denote H, C$_{1-10}$ alkyl, C$_{1-4}$ alkyl aryl, C$_{1-4}$ alkyl heteroaryl, C$_{1-4}$ alkyl C$_{3-8}$ cycloalkyl, C$_{1-4}$ alkyl heterocyclyl or C$_{3-8}$ cycloalkyl, with the proviso that R$^1$ and R$^2$ do not both denote H,
wherein
said alkyl and cycloalkyl groups may each be saturated or mono- or polyunsaturated; and
said alkyl, aryl, heteroaryl, heterocyclyl and cycloalkyl groups may each be unsubstituted or mono- or polysubstituted; or
R$^1$ and R$^2$ together with the nitrogen to which they are bound form a four- to eight-membered heterocyclic ring, optionally bridged by a C$_1$ or C$_2$ alkyl chain, which may contain a further heteroatom and may be substituted or unsubstituted; and
R$^3$ denotes unsubstituted or mono- or poly-substituted phenyl;
wherein if one of R$^1$ or R$^2$ denotes H, alkyl or phenyl alkyl, the other one of R$^1$ and R$^2$ does not denote a group corresponding to formula X1:

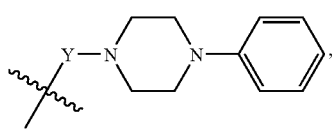

wherein
the phenyl group in formula X1 may be unsubstituted or substituted, and
Y denotes a C$_{2-5}$ alkyl chain or —(CH$_2$)$_o$—Z—(CH$_2$)$_p$—,
wherein
Z denotes cyclopentyl, cyclohexyl or cycloheptyl, and
o and p are each 0, 1, 2 or 3, and the sum of o and p is less than or equal to 3,
or a salt thereof with a physiologically acceptable acid.

2. A compound as claimed in claim 1, wherein said compound is in the form of an isolated stereoisomer.

3. A compound as claimed in claim 1, wherein said compound is in the form of a mixture of stereoisomers in any mixing ratio.

4. A compound as claimed in claim 3, wherein said mixture is a racemic mixture.

5. A compound as claimed in claim 1, wherein:
"alkyl substituted", "heterocyclyl substituted" and "cycloalkyl substituted" denote the replacement of a hydrogen with F, Cl, Br, l, —CN, NH$_2$, NH—C$_{1-6}$ alkyl, NH—C$_{1-6}$ alkyl-OH, C$_{1-6}$ alkyl, N(C$_{1-6}$ alkyl)$_2$, alkyl-OH)$_2$, NO$_2$, SH, S—C$_{1-6}$ alkyl, S-benzyl, O—C$_{1-6}$ alkyl, OH, O—C$_{1-6}$ alkyl-OH, =O, O-benzyl, C(=O)C$_{1-6}$ alkyl, C(=O)OC$_{1-6}$ alkyl, phenyl or benzyl;
"aryl substituted", "phenyl substituted" and "heteroaryl substituted" denote the single or multiple substitution of one or more hydrogen atoms in the ring system with F, Cl, Br, l, CN, NH$_2$, NH—C$_{1-6}$ alkyl, NH—C$_{1-6}$ alkyl-OH, N(C$_{1-6}$ alkyl)$_2$, N(C$_{1-6}$ alkyl-OH)$_2$, NO$_2$, SH, S—C$_{1-6}$ alkyl, OH, O—C$_{1-6}$ alkyl, O-C$_{1-6}$ alkyl-OH, C(=O) aryl;
C(=O)C$_{1-6}$ alkyl, C(=O)NHC$_{1-6}$ alkyl; C(=O)-N-morpholine; C(=O)-piperidine; (C=O)-pyrrolidine; (C=O)-piperazine; NHSO$_2$C$_{1-6}$ alkyl, NHCOC$_{1-6}$ alkyl, CO$_2$H, CH$_2$SO$_2$ phenyl, CO$_2$—C$_{1-6}$ alkyl, OCF$_3$, CF$_3$,

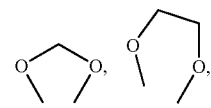

C$_{1-6}$ alkyl, pyrrolidinyl, piperidinyl, morpholinyl, benzyloxy, phenoxy, phenyl, pyridyl, alkylaryl, thienyl or furyl; and
wherein said C$_{1-6}$ alkyl, pyrrolidinyl, piperidinyl, morpholinyl, benzyloxy, phenoxy, phenyl, pyridyl, alkylaryl, thienyl and furyl groups may themselves be substituted with F, Cl, methoxy, ethoxy, CF$_3$, CN, CH$_3$, OH, OCF$_3$, SCF$_3$ or NO$_2$.

6. A compound as claimed in claim 1, wherein R$^1$ and R$^2$ each independently denote C$_{1-10}$ alkyl, C$_{1-4}$ alkyl aryl, C$_{1-4}$ alkyl heteroaryl, C$_{1-4}$ alkyl C$_{3-8}$ cycloalkyl or C$_{3-8}$ cycloalkyl, wherein said alkyl, aryl, heteroaryl and cycloalkyl groups may each be unsubstituted or mono- or polysubstituted.

7. A compound as claimed in claim 6, wherein R$^1$ and R$^2$ each independently denote H, benzyl, phenethyl, methylpyridyl, cyclopropyl, n-pentyl, n-butyl, n-hexyl, sec-butyl, propylethyl or methylcyclohexyl, and each may be unsubstituted or mono- or polysubstituted with methoxy, F, $CH_3$, $CF_3$ or

8. A compound as claimed in claim 1, wherein $R^1$ and $R^2$ together with the nitrogen to which they are bound form a four- to eight-membered ring, optionally bridged by a $C_1$ or $C_2$ alkyl chain, which may contain a further heteroatom selected from the group consisting of O, N and S, and which may be substituted or unsubstituted.

9. A compound as claimed in claim 8, wherein $R^1$ and $R^2$ together with the nitrogen atom to which they are bound form a five- to seven-membered ring which may contain a further nitrogen atom and which may be unsubstituted or mono- or polysubstituted with $C(O)OC_2H_5$; $C(O)C_{1-6}$ alkyl; methyl, n-butyl or acetyl; phenyl or benzyl, which each may be unsubstituted or substituted with phenyl F, Cl, Br, l, CN, $CH_3$, $C_2H_5$, $NH_2$, $NO_2$, SH, $CF_3$, OH, $OCH_3$, $OCF_3$, $SCF_3$, $SCH_3$, $OC_2H_5$ or $N(CH_3)_2$.

10. A compound as claimed in claim 1, wherein $R^3$ denotes a phenyl group, which may be unsubstituted or mono- or polysubstituted with F, Cl, Br, l, CN, $CH_3$, $C_2H_5$, $NH_2$, $NO_2$, SH, $CF_3$, OH, $OCH_3$, $OCF_3$, $SCF_3$, $SCH_3$, phenoxy, $OC_2H_5$ or $N(CH_3)_2$.

11. A compound as claimed in claim 1, selected from the group consisting of:
1 (4-Benzylpiperidin-1-yl)(6-phenyl-5,6,7,8-tetrahydroimidazo[1,2-a]pyridin-2-yl) methanone;
2 N-Benzyl-N-phenethyl-6-phenyl-5,6,7,8-tetrahydroimidazo[1,2-a]pyridine-2-carboxamide;
3 (6-Phenyl-5,6,7,8-tetrahydroimidazo[1,2-a]pyridin-2-yl)(1,3,3-trimethyl-6-azabicyclo [3.2.1]octan-6-yl) methanone;
4 (6-(3-Fluorophenyl)-5,6,7,8-tetrahydroimidazo[1,2-a] pyridin-2-yl)(1,3,3-trimethyl-6-azabicyclo[3.2.1]octan-6-yl)methanone;
5 N-Benzyl-6-(4-methoxy-3,5-dimethylphenyl)-5,6,7,8-tetrahydroimidazo[1,2-a ]pyridine-2-carboxamide;
6 (4-(2-Fluorophenyl)piperazin-1-yl)(6-(4-methoxy-3,5-dimethylphenyl)-5,6,7,8-tetrahydroimidazo [1,2-a]pyridin-2-yl)methanone;
7 (6-(5-Fluoro-2-methoxyphenyl)-5,6,7,8-tetrahydroimidazo[1,2-a]pyridin-2-yl)(4-(3-(trifluoromethyl) phenyl) piperazin-1-yl)methanone;
8 (4-Benzylpiperidin-1-yl)(6-(5-fluoro-2-methoxyphenyl)-5,6,7,8-tetrahydroimidazo [1,2-a]pyridin-2-yl) methanone;
9 (6-(5-Fluoro-2-methoxyphenyl)-5,6,7,8-tetrahydroimidazo[1,2-a]pyridin-2-y 1)(1,3,3-trimethyl-6-azabicyclo [3.2.1]octan-6-yl)methanone;
10 (6-(4-Methoxy-3,5-dimethylphenyl)-5,6,7,8-tetrahydroimidazo[1,2-a]pyridin-2-y 1)(4-(2-methoxyphenyl) piperazin-1-yl)methanone;
11 (4-Benzylpiperidin-1-yl)(6-(4-ethylphenyl)-5,6,7,8-tetrahydroimidazo[1,2-a ]pyridin-2-yl)methanone;
12 (6-(2,5-Dimethoxyphenyl)-5,6,7,8-tetrahydroimidazo [1,2-a]pyridin-2-yl)(1,3,3-trimethyl -6-azabicyclo [3.2.1]octan-6-yl)methanone;
13 (6-(4-Fluoro-3-methylphenyl)-5,6,7,8-tetrahydroimidazo[1,2-a]pyridin-2-yl)(4-(2-fluorophenyl) piperazin-1-yl)methanone;
14 6-(4-Fluoro-3-methylphenyl)-N-(1-phenylethyl)-5,6,7, 8-tetrahydroimidazo[1,2-a ]pyridine-2-carboxamide;
15 6-(4-Methoxy-3,5-dimethylphenyl)-N-pentyl-5,6,7,8-tetrahydroimidazo[1,2-a ]pyridine-2-carboxamide;
16 N-Hexyl-6-(4-methoxy-3,5-dimethylphenyl)-5,6,7,8-tetrahydroimidazo[1,2-a ]pyridine-2-carboxamide;
17 6-(4-Methoxy-3,5-dimethylphenyl)-N-(3-(trifluoromethyl)benzyl)-5,6,7,8-tetrahydroimidazo [1,2-a]pyridine-2-carboxamide;
18 N-sec-Butyl-6-(4-phenoxyphenyl)-5,6,7,8-tetrahydroimidazo[1,2-a]pyridine-2-carboxamide;
19 N-Butyl-6-(4-phenoxyphenyl)-5,6,7,8-tetrahydroimidazo[1,2-a]pyridine-2-carboxamide;
20 Ethyl 1-(6-(4-phenoxyphenyl)-5,6,7,8-tetrahydroimidazo[1,2-a]pyridine-2-carbonyl) piperidine-4-carboxylate;
21 (4-Methylpiperidin-1-yl)(6-(4-phenoxyphenyl)-5,6,7, 8-tetrahydroimidazo[1,2-a ]pyridin-2-yl)methanone;
22 Ethyl 1-(6-(4-phenoxyphenyl)-5,6,7,8-tetrahydroimidazo[1,2-a]pyridine-2-carbonyl) piperidine-3-carboxylate;
23 1-(4-(6-(4-Phenoxyphenyl)-5,6,7,8-tetrahydroimidazo [1,2-a]pyridine-2-carbonyl) piperazin-1-ypethanone;
24 6-(4-Phenoxyphenyl)-N-(pyridin-3-ylmethyl)-5,6,7,8-tetrahydroimidazo[1,2-a ]pyridine-2-carboxamide;
25 (6-(4-Phenoxyphenyl)-5,6,7,8-tetrahydroimidazo[1,2-a]pyridin-2-yl)(pyrrolidin-1-yl) methanone;
26 N-Cyclopropyl-6-(4-phenoxyphenyl)-5,6,17,8-tetrahydroimidazo[1,2-a]pyridine-2-carboxamide;
27 N-(3,4-Dimethoxyphenethyl)-6-(4-phenoxyphenyl)-5, 6,7,8-tetrahydroimidazo[1,2-a ]pyridine-2-carboxamide;
28 N-Pentyl-6-(4-phenoxyphenyl)-5,6,7,8-tetrahydroimidazo[1,2-a]pyridine-2-carboxamide;
29 Pyrrolidin-1-yl(6-m-tolyl-5,6,7,8-tetrahydroimidazo [1,2-a]pyridin-2-yl)methanone;
30 (6-(3,5-Bis(trifluoromethyl)phenyl)-5,6,7,8-tetrahydroimidazo[1,2-a]pyridin-2-yl) (pyrrolidin-1-yl)methanone;
31 Pyrrolidin-1-yl(6-(3-(trifluoromethyl)phenyl)-5,6,7,8-tetrahydroimidazo[1,2-a ]pyridin-2-yl)methanone;
32 (4-(2-Fluorophenyl)piperazin-1-yl)(6-(3-(trifluoromethyl)phenyl)-5,6,7,8-tetrahydroimidazo [1,2-a]pyridin-2-yl)methanone;
33 (6-(2,4-Dimethoxyphenyl)-5,6,7,8-tetrahydroimidazo [1,2-a]pyridin-2-yl)(pyrrolidin-1-yl)methanone;
34 Pyrrolidin-1-yl(6-o-tolyl-5,6,7,8-tetrahydroimidazo[1, 2-a]pyridin-2-yl)methanone;
35 (6-o-Tolyl-5,6,7,8-tetrahydroimidazo[1,2-a]pyridin-2-yl)(4-(3-(trifluoromethyl)-phenyl) piperazin-1-yl) methanone;
36 (6-(2,5-Difluorophenyl)-5,6,7,8-tetrahydroimidazo[1, 2-a]pyridin-2-yl)(pyrrolidin-1-yl methanone;
37 (6-(4-Ethylphenyl)-5,6,7,8-tetrahydroimidazo[1,2-a] pyridin-2-yl)(pyrrolidin-1-yl) methanone;
38 (6-(4-Fluorophenyl)-5,6,7,8-tetrahydroimidazo[1,2-a] pyridin-2-yl)(1,3,3-trimethyl-6-azabicyclo[3.2.1]octan-6-yl)methanone;
39 6-(4-Methoxyphenyl)-N-(3-(trifluoromethyl)benzyl)-5,6,7,8-tetrahydroimidazo[1,2-a ]pyridine-2-carboxamide;
40 6-(4-Ethylphenyl)-N-phenethyl-5,6,7,8-tetrahydroimidazo[1,2-a]pyridine-2-carboxamide;
41 (4-Benzylpiperidin-1-yl)(6-(4-fluorophenyl)-5,6,7,8-tetrahydroimidazo[1,2-a ]pyridin-2-yl)methanone;
42 N-(Benzo[d][1,3]dioxo1-5-ylmethyl)-6-(3,5-bis(trifluoromethyl)phenyl)-5,6,7,8-tetrahydroimidazo [1,2-a] pyridine-2-carboxamide;

43 N-Benzyl-6-(3,5-bis(trifluoromethyl)phenyl)-5,6,7,8-tetrahydroimidazo[1,2-a]pyridine-2-carboxamide;

44 (6-(4-Methoxy-3,5-dimethylphenyl)-5,6,7,8-tetrahydroimidazo[1,2-a]pyridin-2-yl) (4-(4-methoxyphenyl)piperazin-1-yl)methanone;

45 (4-(2-Ethoxyphenyl)piperazin-1-yl)(6-m-tolyl-5,6,7,8-tetrahydroimidazo[1,2-a]pyridin-2-yl)methanone;

46 (6-(2,4-Dimethoxyphenyl)-5,6,7,8-tetrahydroimidazo[1,2-a]pyridin-2-yl)(4-(3-(trifluoromethyl) phenyl)piperazin-1-yl)methanone;

47 (6-(4-Fluorophenyl)-5,6,7,8-tetrahydroimidazo[1,2-a]pyridin-2-yl)(4-(3-(trifluoromethyl) phenyl)piperazin-1-yl)methanone;

48 (6-(3-Fluorophenyl)-5,6,7,8-tetrahydroimidazo[1,2-a]pyridin-2-yl)(4-(3-(trifluoromethyl) phenyl)piperazin-1-yl)methanone;

49 N-(4-Fluorobenzyl)-6-(4-methoxy-3,5-dimethylphenyl)-5,6,7,8-tetrahydroirnidazo-[1,2-a]pyridine-2-carboxamide;

50 (4-Benzylpiperidin-1-yl)(6-(3-methoxyphenyl)-5,6,7,8-tetrahydroimidazo[1,2-a]pyridin-2-yl)methanone;

51 6-(3-Fluorophenyl)-N-(4-phenylbutan-2-yl)-5,6,7,8-tetrahydroimidazo[1,2-a]pyridine-2-carboxamide;

52 6-(4-Ethylphenyl)-N-(4-phenylbutan-2-yl)-5,6,7,8-tetrahydroimidazo[1,2-a]pyridine-2-carboxamide;

53 (6-Phenyl-5,6,7,8-tetrahydroimidazo[1,2-a]pyridin-2-yl)(4-(3-(trifluoromethyl) phenyl)piperazin-1-yl)methanone;

54 (6-(4-Methoxy-3,5-dimethylphenyl)-5,6,7,8-tetrahydroimidazo[1,2-a]pyridin-2-yl) (4-(3-(trifluoromethyl)phenyl)piperazin-1-yl)methanone;

55 (4-Benzylpiperidin-1-yl)(6-(4-methoxy-3,5-dimethylphenyl)-5,6,7,8-tetrahydro-imidazo [1,2-a]pyridin-2-yl)methanone;

56 (6-(4-Methoxy-3,5-dimethylphenyl)-5,6,7,8-tetrahydroimidazo[1,2-a]pyridin-2-y) (1,3,3-trimethyl-6-azabicyclo[3.2.1]octan-6-yl)methanone;

57 4-Benzylpiperidin-1-yl)(6-(4-fluoro-3-methylphenyl)-5,6,7,8-tetrahydroimidazo [1,2-a]pyridin-2-yl)methanone;

58 (6-(4-Fluoro-3-methylphenyl)-5,6,7,8-tetrahydroimidazo[1,2-a]pyridin-2-yl)(4-(3-(trifluoromethyl) phenyl)piperazin-1-yl)methanone;

59 (4-Benzhydrylpiperazin-1-yl)(6-(4-methoxy-3,5-dimethylphenyl)-5,6,7,8-tetrahydroimidazo [1,2-a]pyridin-2-yl)methanone;

60 6-(3-Methoxyphenyl)-N-(4-phenylbutan-2-yl)-5,6,7,8-tetrahydroimidazo[1,2-a]pyridine-2-carboxamide;

61 (4-Benzylpiperidin-1-yl)(6-(3-fluorophenyl)-5,6,7,8-tetrahydroimidazo[1,2-a]pyridin-2-yl)methanone;

62 (6-(4-Fluoro-3-methylphenyl)-5,6,7,8-tetrahydroimidazo[1,2-a]pyridin-2-yl)(4-(4-(trifluoromethyl) phenyppiperazin-1-yl)methanone;

63 (6-(4-Fluoro-3-methylphenyl)-5,6,7,8-tetrahydroimidazo[1,2-a]pyridin-2-yl)(4-(4-fluorophenyl) piperazin-1-yl)methanone;

64 (6-(4-Fluoro-3-methylphenyl)-5,6,7,8-tetrahydroimidazo[1,2-a]pyridin-2-yl)(4-(4-methylphenyl) piperazin-1-Arnethanone;

65 (6-(4-Fluoro-3-methylphenyl)-5,6,7,8-tetrahydroimidazo[1,2-a]pyridin-2-yl)(4-(3-methylphenyl) piperazin-1-yl)methanone;

66 (4-Butylpiperazin-1-yl)(6-(4-fluoro-3-methylphenyl)-5,6,7,8-tetrahydroimidazo [1,2-a]pyridin-2-ylynethanone;

67 (4-Benzhydrylpiperidin-1-yl)(6-(4-fluoro-3-methylphenyl)-5,6,7,8-tetrahydro-imidazo [1,2-a]pyridin-2-yl)methanone;

68 N-(Cyclohexylmethyl)-6-(4-fluoro-3-methylphenyl)-5,6,7,8-tetrahydroimidazo[1,2-a]pyridine-2-carboxamide;

69 (6-(4-Methoxyphenyl)-5,6,7,8-tetrahydroimidazo[1,2-a]pyridin-2-yl)(4-(3-(trifluoromethyl) phenyl)piperazin-1-yl)methanone;

70 (4-Benzylpiperidin-1-yl)(6-m-tolyl-5,6,7,8-tetrahydroimidazo[1,2-a]pyridin-2-yl) methanone;

71 (6-(3-Methoxyphenyl)-5,6,7,8-tetrahydroimidazo[1,2-a]pyridin-2-yl)(4-(3-(trifluoromethyl) phenyppiperazin-1-yl)methanone;

72 6-(4-Fluoro-3-methylphenyl)-N-(4-phenylbutan-2-yl)-5,6,7,8-tetrahydroimidazo-[1,2-a]pyridine-2-carboxamide;

73 4-Benzylpiperidin-1-yl)(6-p-tolyl-5,6,7,8-tetrahydroimidazo[1,2-a]pyridin-2-yl) methanone;

74 (6-p-Tolyl-5,6,7,8-tetrahydroimidazo[1,2-a]pyridin-2-yl)(4-(3-(trifluoromethyl)-phenyl) piperazin-1-Amethanone;

75 (6-m-Tolyl-5,6,7,8-tetrahydroimidazo[1,2-a]pyridin-2-yl)(4-(3-(trifluoromethyl)-phenyl) piperazin-1-yl)methanone;

76 (4-Benzylpiperidin-1-yl)(6-(4-methoxyphenyl)-5,6,7,8-tetrahydroimidazo[1,2-a]pyridin-2-yl)methanone;

77 (6-(3,5-Dimethylphenyl)-5,6,7,8-tetrahydroimidazo[1,2-a]pyridin-2-yl)(4-(3-(trifluoromethypphenyl) piperazin-1-yl)methanone;

78 N-(1-(3,5-Dimethylphenypethyl)-6-(4-fluoro-3-methylphenyl)-5,6,7,8-tetrahydroimidazo [1,2-a]pyridine-2-carboxamide;

79 6-(3,4-Difluorophenyl)-5,6,7,8-tetrahydroimidazo[1,2-a]pyridin-2-yl)(4-(3-(trifluoromethyl) phenyl)piperazin-1-yl)methanone;

80 (4-Benzylpiperazin-1-yl)(6-(4-fluoro-3-methylphenyl)-5,6,7,8-tetrahydro-imidazo [1,2-a]pyridin-2-yl) methanone;

81 (6-(4-Phenoxyphenyl)-5,6,7,8-tetrahydroimidazo[1,2-a]pyridin-2-yl)(4-(3-(trifluoromethyl) phenyppiperazin-1-yDrnethanone;

82 6-(4-(Benzyloxy)phenyl)-5,6,7,8-tetrahydroimidazo [1,2-a]pyridin-2-yl)(4-(3-(trifluoromethyl) phenyppiperazin-1-yl)methanone;

83 (6-(4-Fluoro-3-methylphenyl)-5,6,7,8-tetrahydroimidazo[1,2-a]pyridin-2-yl)(4-(3-fluorophenyl) piperazin-1-yl)methanone;

84 (6-(4-Fluoro-3-methylphenyl)-5,6,7,8-tetrahydroimidazo[1,2-a]pyridin-2-yl)(1,3,3-trimethyl-6-azabicyclo [3.2.1]octan-6-yl)methanone;

85 (6-(4-Fluoro-3-methylphenyl)-5,6,7,8-tetrahydroimidazo[1,2-a]pyridin-2-yl)(4-(3-(trifluoromethyl) phenyl) piperidin-1-yl)methanone;

86 6-(4-Fluoro-3-methylphenyl)-N-(4-(3-(trifluoromethyl)phenyl)butan-2-yO-5,6,7,8-tetrahydroimidazo [1,2-a]pyridine-2-carboxamide;

87 6-(4-Fluoro-3-methylphenyl)-N-methyl-N-(4-(3-(trifluoromethyl)phenyl)butan-2-yl) -5,6,7,8-tetrahydroimidazo[1,2-a]pyridine-2-carboxamide; and 88 N-(2-Cyclohexylethyl)-6-(4-fluoro-3-methylphenyl)-5,6,7,8-tetrahydroimidazo[1,2-a]pyridine-2-carboxamide.

12. A pharmaceutical composition comprising a compound as claimed in claim 1, and at least one pharmaceutically acceptable carrier or auxiliary substance.

13. A method of treating pain in a subject, said method comprising administering to said subject a pharmacologically effective amount of a compound as claimed in claim 1.

14. A method as claimed in claim 13, wherein said pain is selected from the group consisting of acute pain, chronic pain, neuropathic pain, muscular pain and inflammatory pain.

15. A method of treating a condition selected from the group consisting of pain, epilepsy, migraine, anxiety and urinary incontinence in a subject, said method comprising administering to said subject a pharmacologically effective amount of a compound as claimed in claim 1.

16. A process for preparing a compound as claimed in claim 1, according to the following reaction scheme:

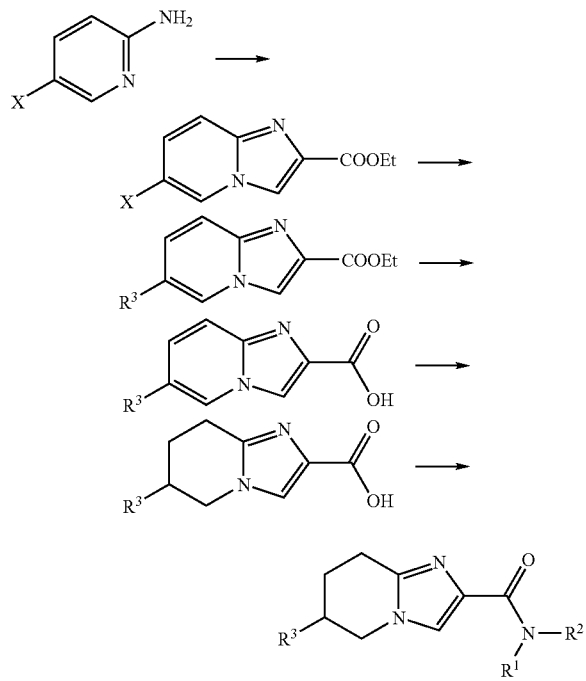

X = Cl, Br, I said process comprising:
a) reacting an iodine-, bromine- or chlorine-substituted 2-aminopyridine with 3-bromo -2-oxopropionic acid in an organic solvent at a temperature between 0° C. and 80° C. for 2 to 48 hours to yield an iodine-, bromine- or chlorine-substituted imidazo[1,2-a]pyridine-2-carboxylic acid ethyl ester;
b) reacting the iodine-, bromine- or chlorine-substituted imidazo[1,2-a]pyridine-2-carboxylic acid ethyl ester from a) with a phenylboric acid or phenylboric acid ester in a solvent using a catalyst, a base and optionally an additive;
c) cleaving the carboxylic acid ester using an organic or aqueous inorganic acid or an aqueous inorganic base in an organic solvent to yield a substituted imidazopyridine carboxylic acid;
d) hydrogenating the substituted imidazopyridine carboxylic acid from c) with a hydrogenation catalyst in a solvent under normal pressure or elevated pressure to yield a tetrahydroimidazopyridine carboxylic acid; and
e) reacting the tetrahydroimidazopyridine carboxylic acid from d) with a primary or secondary amine using a base, and optionally a coupling reagent, in a solvent.

17. A process as claimed in claim 16, wherein:
said solvents are independently selected from the group consisting of methanol, ethanol, 1-propanol, ethylene glycol, water, THF, 1,2-dimethoxyethane, acetone, chloroform, dioxane, acetonitrile, DMF, benzene, toluene, xylene, dichloromethane, diethyl ether, acetic acid, propionic acid, DCM, cyclohexane or methanolic KOH;
said carboxylic acid ester is cleaved with trifluoroacetic acid or aqueous hydrochloric acid or an aqueous based selected from the group consisting of lithium hydroxide, potassium hydroxide, sodium hydroxide, sodium carbonate, sodium hydrogen carbonate or potassium carbonate;
said hydrogenation catalyst is selected from the group consisting of Pd on activated carbon, Raney nickel, platinum or $PtO_2$;
said base is selected from the group consisting of sodium methanolate, TEA, DIEA or N-methylmorpholine; and
said coupling reagent is selected from the group consisting of EDCI, HOBt, DCC, CDI, HBTU, DMAP or pentafluorophenyl diphenyl phosphinate.

* * * * *